US011395821B2

(12) United States Patent
Sorrentino et al.

(10) Patent No.: US 11,395,821 B2
(45) Date of Patent: Jul. 26, 2022

(54) TREATMENT OF EGFR-DRIVEN CANCER WITH FEWER SIDE EFFECTS

(71) Applicant: G1 Therapeutics, Inc., Research Triangle Park, NC (US)

(72) Inventors: Jessica A. Sorrentino, Durham, NC (US); Jay Copeland Strum, Hillsborough, NC (US); John E. Bisi, Apex, NC (US); Andrew Beelen, Research Triangle Park, NC (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 16/547,342

(22) Filed: Aug. 21, 2019

(65) Prior Publication Data

US 2019/0374545 A1 Dec. 12, 2019

Related U.S. Application Data

(63) Continuation of application No. PCT/US2018/019291, filed on Feb. 22, 2018.

(60) Provisional application No. 62/452,094, filed on Jan. 30, 2017.

(51) Int. Cl.
| | |
|---|---|
| *A61K 31/519* | (2006.01) |
| *A61K 31/506* | (2006.01) |
| *A61K 31/5377* | (2006.01) |
| *A61P 35/00* | (2006.01) |
| *A61K 31/4709* | (2006.01) |
| *A61K 31/517* | (2006.01) |

(52) U.S. Cl.
CPC ........ *A61K 31/519* (2013.01); *A61K 31/4709* (2013.01); *A61K 31/506* (2013.01); *A61K 31/517* (2013.01); *A61K 31/5377* (2013.01); *A61P 35/00* (2018.01)

(58) Field of Classification Search
CPC ................ A61K 31/519; A61K 31/506; A61K 31/5377; A61P 35/00
See application file for complete search history.

(56) References Cited

U.S. PATENT DOCUMENTS

| | | | |
|---|---|---|---|
| 8,232,062 B2 | 7/2012 | Seshagiri | |
| 8,598,186 B2 | 12/2013 | Tavares et al. | |
| 8,598,197 B2 | 12/2013 | Tavares et al. | |
| 8,691,830 B2 | 4/2014 | Tavares et al. | |
| 8,822,683 B2 | 9/2014 | Tavares et al. | |
| 8,829,012 B2 | 9/2014 | Tavares et al. | |
| 8,987,266 B2 | 3/2015 | Seshagiri | |
| 9,102,682 B2 | 8/2015 | Tavares et al. | |
| 9,108,929 B2 | 8/2015 | Qian et al. | |
| 9,260,442 B2 | 2/2016 | Tavares | |
| 9,464,092 B2 | 10/2016 | Strum et al. | |
| 9,481,691 B2 | 11/2016 | Tavares et al. | |
| 9,487,530 B2 | 11/2016 | Strum et al. | |
| 9,499,564 B2 | 11/2016 | Tavares et al. | |
| 9,527,857 B2 | 12/2016 | Strum et al. | |
| 9,683,048 B2 | 6/2017 | Freeman et al. | |
| 9,700,557 B2 | 7/2017 | Caponigro et al. | |
| 9,717,735 B2 | 8/2017 | Strum et al. | |
| 9,745,316 B2 | 8/2017 | Tavares | |
| 10,231,969 B2 | 3/2019 | Strum et al. | |
| 2011/0009353 A1 | 1/2011 | Chen-Kiang et al. | |
| 2011/0224221 A1 | 9/2011 | Sharpless et al. | |
| 2011/0224227 A1 | 9/2011 | Sharpless et al. | |
| 2011/0294686 A1 | 12/2011 | Drabkin et al. | |
| 2012/0100100 A1 | 4/2012 | Sharpless et al. | |
| 2014/0011821 A1 | 1/2014 | Seshagiri | |
| 2014/0107114 A1 | 4/2014 | Kim et al. | |
| 2014/0271460 A1 | 9/2014 | Sharpless et al. | |
| 2014/0271466 A1 | 9/2014 | Sharpless et al. | |
| 2014/0274896 A1 | 9/2014 | Sharpless et al. | |
| 2014/0275066 A1 | 9/2014 | Sharpless et al. | |
| 2014/0275067 A1 | 9/2014 | Sharpless et al. | |
| 2014/0314747 A1 | 10/2014 | Strasser et al. | |
| 2015/0031880 A1 | 1/2015 | Tavares et al. | |
| 2015/0246925 A1 | 9/2015 | Tavares et al. | |
| 2015/0246926 A1 | 9/2015 | Tavares et al. | |
| 2015/0297606 A1 | 10/2015 | Strum et al. | |
| 2015/0297607 A1 | 10/2015 | Strum et al. | |
| 2015/0297608 A1 | 10/2015 | Strum et al. | |

(Continued)

FOREIGN PATENT DOCUMENTS

| | | |
|---|---|---|
| WO | WO 2005/117877 A1 | 12/2005 |
| WO | WO 2005/117887 A1 | 12/2005 |

(Continued)

OTHER PUBLICATIONS

G1 Therapeutics Press Releases, Nov. 2017, pp. 1-4.*
Beck et al., EGFR and Rb1 as dual biomarkers in HPV-negative Head & Neck Cancer, Mol. Cancer Ther., Oct. 2016, 15(10): 2486-2497.
Cross et al., AZD9291, an irreversible EGFR TKI, overcomes T790M-mediated resistance to EGFR inhibitors in lung cancer; Cancer Discov. Sep. 2014; 4 (9): 1046-1061. doi:10.1158/2159-8290.CD-14-0337.
Eberlein et al., Acquired Resistance to the Mutant-Selective EGFR Inhibitor AZD9291 is Associated with Increased Dependence on RAS Signaling in Preclinical Models; Cancer Res; 75(12) Jun. 15, 2015: 2489-2500. doi: 10.1158/0008-5472.CAN-14-3167.

(Continued)

*Primary Examiner* — Samira J Jean-Louis
(74) *Attorney, Agent, or Firm* — Knowles Intellectual Property Strategies, LLC

(57) ABSTRACT

The present invention provides methods for treating a EGFR-mutant cancer in a patient by administering a selective CDK4/6 inhibitor described herein in combination or alternation with an EGFR-TKI to delay or reverse acquired resistance to previously administered EGFR-TKIs. In addition, methods for treating a EGFR-mutant cancer in a patient by administering a selective CDK4/6 inhibitor described herein in combination or alternation with an EGFR-TKI are provided wherein an intrinsically EGFR-TKI resistant EGFR-mutant cancer is sensitized to the effects of the EGFR-TKI.

7 Claims, 6 Drawing Sheets

(56) References Cited

U.S. PATENT DOCUMENTS

| | | |
|---|---|---|
| 2015/0299212 A1 | 10/2015 | Strum et al. |
| 2016/0045509 A1 | 2/2016 | Strum et al. |
| 2016/0220569 A1 | 8/2016 | Strum et al. |
| 2016/0310499 A1 | 10/2016 | Strum et al. |
| 2016/0332969 A1 | 11/2016 | Kuntz et al. |
| 2016/0332989 A1 | 11/2016 | Wu et al. |
| 2017/0037051 A1 | 2/2017 | Strum et al. |
| 2017/0057971 A1 | 3/2017 | Tavares et al. |
| 2017/0057972 A1 | 3/2017 | Tavares |
| 2017/0065597 A1 | 3/2017 | Strum et al. |
| 2017/0100405 A1 | 4/2017 | Strum et al. |
| 2017/0119774 A1 | 5/2017 | Strum et al. |
| 2017/0224819 A1 | 8/2017 | Hamdy et al. |
| 2017/0296659 A1 | 10/2017 | Lebwohl et al. |
| 2018/0243304 A1 | 8/2018 | Caponigro et al. |
| 2018/0318305 A1 | 11/2018 | Harris et al. |
| 2018/0360840 A1 | 12/2018 | Strum et al. |
| 2019/0030034 A1 | 1/2019 | Strum et al. |
| 2019/0070185 A1 | 3/2019 | Strum et al. |
| 2019/0160066 A1 | 5/2019 | Katayama et al. |
| 2019/0275049 A1 | 9/2019 | Goldberg et al. |

FOREIGN PATENT DOCUMENTS

| | | | |
|---|---|---|---|
| WO | WO 2005/117915 A1 | 12/2005 | |
| WO | WO 2010/020675 A1 | 2/2010 | |
| WO | WO 2010/039997 A2 | 4/2010 | |
| WO | WO 2010/051127 A2 | 5/2010 | |
| WO | WO 2010/132725 A2 | 11/2010 | |
| WO | WO 2012129344 A1 | 9/2012 | |
| WO | WO 2012/061156 A2 | 10/2012 | |
| WO | WO 2013/014448 A1 | 1/2013 | |
| WO | WO 2013/148748 A1 | 10/2013 | |
| WO | WO 2013/163239 A1 | 10/2013 | |
| WO | WO 2014/140989 A2 | 9/2014 | |
| WO | WO 2014/144326 A1 | 9/2014 | |
| WO | WO 2014/144596 A2 | 9/2014 | |
| WO | WO 2014/144740 A2 | 9/2014 | |
| WO | WO 2014/144847 A2 | 9/2014 | |
| WO | WO 2015/061407 A1 | 4/2015 | |
| WO | WO 2015081463 A1 | 6/2015 | |
| WO | WO 2015085482 A1 | 6/2015 | |
| WO | WO 2015/153866 A1 | 10/2015 | |
| WO | WO 2015/161283 A1 | 10/2015 | |
| WO | WO 2015/161285 A1 | 10/2015 | |
| WO | WO 2015/161287 A1 | 10/2015 | |
| WO | WO 2015/161288 A1 | 10/2015 | |
| WO | WO 2016/040848 A1 | 3/2016 | |
| WO | WO 2016/040858 A1 | 3/2016 | |
| WO | WO 2016/040882 A1 | 3/2016 | |
| WO | WO 2016059600 A1 | 4/2016 | |
| WO | WO 2016/079763 A1 | 5/2016 | |
| WO | WO 2016/126889 A1 | 8/2016 | |
| WO | WO 2017/037576 A1 | 3/2017 | |
| WO | WO 2017/160568 A1 | 9/2017 | |
| WO | WO 2017/193141 A1 | 11/2017 | |
| WO | WO 2017/222958 A1 | 12/2017 | |
| WO | WO 2018/091999 A1 | 5/2018 | |
| WO | WO 2018/099952 A1 | 6/2018 | |
| WO | WO 2018/106729 A1 | 6/2018 | |
| WO | WO 2018/156812 A1 | 8/2018 | |
| WO | WO 2018/218633 A1 | 12/2018 | |

OTHER PUBLICATIONS

Engelman et al., Mechanisms of Acquired Resistance to Epidermal Growth Factor Receptor Tyrosine Kinase Inhibitors in Non-Small Cell Lung Cancer; Clin Cancer Res 2895 2008; 14 (10) May 15, 2008. doi: 10.1158/1078-0432.CCR-07-2248.

Ercan et al., EGFR Mutations and Resistance to Irreversible Pyrimidine-Based EGFR Inhibitors; Clin Cancer Res; 21(17) Sep. 1, 2015; Published Online First May 6, 2015; doi: 10.1158/1078-0432.CCR-14-2789.

Janne et al., AZD9291 in EGFR Inhibitor-Resistant Non-Small-Cell Lung Cancer; N Engl J Med 2015; 372: 1689-99. DOI: 10.1056/NEJMoa1411817.

Kim et al., Mechanisms of Acquired Resistance to AZD9291 A Mutation-Selective, Irreversible EGFR Inhibitor; J Thorac Oncol. 2015;10: 1736-1744. DOI: 10.1097/JTO.0000000000000688.

Kohler et al., Afatinib, Erlotinib and Gefitinib in the First-Line Therapy of EGFR Mutation-Positive Lung Adenocarcinoma: A Review; Onkologie 2013; 36: 510-518 Published online: Aug. 19, 2013. DOI: 10.1159/000354627.

Liao et al., Update on recent preclinical and clinical studies of T790M mutant-specific irreversible epidermal growth factor receptor tyrosine kinase inhibitors; Journal of Biomedical Science (2016) 23: 86. DOI 10.1186/s12929-016-0305-9.

Liu et al., PD 0332991, a selective cyclin D kinase 4/6 inhibitor, sensitizes lung cancer cells to treatment with epidermal growth factor receptor tyrosine kinase inhibitors; Oncotarget, 2016, vol. 7, (No. 51), pp. 84951-84964.

Naumov et al., Combined Vascular Endothelial Growth Factor Receptor and Epidermal Growth Factor Receptor (EGFR) Blockade Inhibits Tumor Growth in Xenograft Models of EGFR Inhibitor Resistance; Clin Cancer Res 2009; 15 (10) May 15, 2009. doi: 10.1158/1078-0432.CCR-08-2904.

Niederst et al., The Allelic Context of the C797S Mutation Acquired upon Treatment with Third-Generation EGFR Inhibitors Impacts Sensitivity to Subsequent Treatment Strategies; Clin Cancer Res; 21 (17) Sep. 1, 2015. doi: 0.1158/1078-0432.CCR-15-0560.

Ohashi et al., Epidermal Growth Factor Receptor Tyrosine Kinase Inhibitor-Resistant Disease; J Clin Oncol Mar. 10, 2013 (8) 31:1070-1080. DOI: 10.1200/JCO.2012.43.3912.

Planchard et al., EGFR-independent mechanisms of acquired resistance to AZD9291 in EGFR T790M-positive NSCLC patients; Annals of Oncology 26: 2073-2078, 2015. doi:10.1093/annonc/mdv319. Published online Aug. 12, 2015.

Sos et al., PTEN Loss Contributes to Erlotinib Resistance in EGFR-Mutant Lung Cancer by Activation of Akt and EGFR; Cancer Res. Apr. 15, 2009; 69 (8): 3256-3261. doi: 10.1158/0008-5472.CAN-08-4055.

Thress et al., Acquired EGFR C797S mutation mediates resistance to AZD9291 in non-small cell lung cancer harboring EGFR T790M; Nature Medicine vol. 21 (6) Jun. 2015. published online May 4, 2015; doi:10.1038/nm.3854.

Wang et al., Intrinsic resistance to EGFR tyrosine kinase inhibitors in advanced non-small-cell lung cancer with activating EGFR mutations; OncoTargets and Therapy 2016: 9 3711-3726. doi.org/10.2147/OTT.S106399.

Yates et al., Irreversible Inhibition of EGFR: Modeling the Combined Pharmacokinetic-Pharmacodynamic Relationship of Osimertinib and Its Active Metabolite AZ5104; Mol Cancer Ther; 15(10) Oct. 2016. doi: 10.1158/1535-7163.MCT-16-0142.

Yu et al., Analysis of Tumor Specimens at the Time of Acquired Resistance to EGFR-TKI Therapy in 155 Patients with EGFR-Mutant Lung Cancers; Clin Cancer Res; 19 (8) Apr. 15, 2013. doi: 10.1158/1078-0432.CCR-12-2246.

Zhang et al., Activation of the AXL Kinase Causes Resistance to EGFR-Targeted Therapy in Lung Cancer; Nat Genet.; 44(8): 852-860. doi: 10.1038/ng.2330.

U.S. Pat. No. 8,598,187 B2, U.S. Appl. No. 13/869,576, Tavares et al., Dec. 3, 2013.

U.S. Pat. No. 9,102,682 B2, U.S. Appl. No. 14/152,296, Tavares et al., Aug. 11, 2015.

US, 2018/0127431 A1, U.S. Appl. No. 15/860,483, Tavares et al., May 10, 2018.

US, 2018/0221378 A1, U.S. Appl. No. 15/943,278, Strum, et al., Aug. 9, 2018.

US, 2019/0119292 A1, U.S. Appl. No. 16/226,430, Tavares et al., Apr. 25, 2019.

US, 2019/0119294 A1, U.S. Appl. No. 16/230,412, Strum, et al., Apr. 25, 2019.

US, 2019/0125752 A1, U.S. Appl. No. 16/228,308, Strum, et al., May 2, 2019.

US, 2019/0135784 A1, U.S. Appl. No. 16/230,388, Strum, et al., May 9, 2019.

(56) References Cited

OTHER PUBLICATIONS

US, 2019/0135811 A1, U.S. Appl. No. 16/230,396, Strum, et al., May 9, 2019.
US, 2019/0321370 A1, U.S. Appl. No. 16/432,240, Sorrentino, et al., Oct. 24, 2019.
U.S. Pat. No. 8,598,186 B2, U.S. Appl. No. 13/869,520, Tavares et al., Dec. 3, 2013.
U.S. Pat. No. 8,598,197 B2, U.S. Appl. No. 13/869,576, Tavares et al., Dec. 3, 2013.
U.S. Pat. No. 8,691,830 B2, U.S. Appl. No. 13/869,594, Tavares et al., Apr. 8, 2014.
U.S. Pat. No. 8,822,683 B2, U.S. Appl. No. 14/162,637, Tavares et al., Sep. 2, 2014.
U.S. Pat. No. 8,829,012 B2, U.S. Appl. No. 14/162,649, Tavares et al., Sep. 9, 2014.
U.S. Pat. No. 9,102,682 B2, U.S. Appl. No. 14/452,296, Tavares et al., Aug. 11, 2015.
U.S. Pat. No. 9,260,442 B2, U.S. Appl. No. 14/498,796, Tavares, Jan. 27, 2016.
U.S. Pat. No. 9,464,092 B2, U.S. Appl. No. 14/212,911, Strum et al., Oct. 11, 2016.
U.S. Pat. No. 9,481,691 B2, U.S. Appl. No. 14/712,630, Tavares et al., Nov. 1, 2016.
U.S. Pat. No. 9,487,530 B2, U.S. Appl. No. 14/212,430, Strum et al., Nov. 8, 2016.
U.S. Pat. No. 9,499,564 B2, U.S. Appl. No. 14/712,582, Tavares et al., Nov. 22, 2016.
U.S. Pat. No. 9,527,857 B2, U.S. Appl. No. 14/214,048, Strum et al., Dec. 27, 2016.
U.S. Pat. No. 9,717,735 B2, U.S. Appl. No. 14/690,180, Strum et al., Aug. 1, 2017.
U.S. Pat. No. 9,745,316 B2, U.S. Appl. No. 14/982,443, Tavares, Aug. 29, 2017.
U.S. Pat. No. 9,856,268 B2, U.S. Appl. No. 15/348,862, Tavares, Jan. 2, 2018.
U.S. Pat. No. 9,931,345 B2, U.S. Appl. No. 15/288,878, Strum et al., Apr. 3, 2018.
U.S. Pat. No. 9,957,276 B2, U.S. Appl. No. 15/348,770, Tavares et al., May 1, 2018.
U.S. Pat. No. 10,076,523 B2, U.S. Appl. No. 15/387,083, Strum et al., Sep. 18, 2018.
U.S. Pat. No. 10,085,992 B2, U.S. Appl. No. 15/342,990, Strum et al., Oct. 2, 2018.
U.S. Pat. No. 10,189,849 B2, U.S. Appl. No. 15/918,834, Tavares et al., Jan. 29, 2019.
U.S. Pat. No. 10,189,850 B2, U.S. Appl. No. 15/918,852, Tavares et al., Jan. 29, 2019.
U.S. Pat. No. 10,189,851 B2, U.S. Appl. No. 15/918,877, Tavares et al., Jan. 29, 2019.
U.S. Pat. No. 10,208,011 B2, U.S. Appl. No. 15/893,295, Strum, et al., Feb. 19, 2019.
U.S. Pat. No. 10,231,969 B2, U.S. Appl. No. 15/457,699, Strum, et al., Mar. 19, 2019.
U.S. Pat. No. 10,376,519 B2, U.S. Appl. No. 15/665,071, Strum, et al., Aug. 13, 2019.
U.S. Pat. No. 10,413,547 B2, U.S. Appl. No. 16/142,574, Strum, et al., Sep. 17, 2019.
U.S. Pat. No. 10,434,104 B2, U.S. Appl. No. 16/112,362, Strum, et al., Oct. 8, 2019.
U.S. Pat. No. 10,464,940 B2, U.S. Appl. No. 15/860,483, Tavares et al., Nov. 5, 2019.
U.S. Pat. No. 10,618,905 B2, U.S. Appl. No. 16/230,412, Strum, et al., Apr. 14, 2020.
U.S. Pat. No. 10,633,362 B2, U.S. Appl. No. 16/221,201, Strum, et al., Apr. 28, 2020.
U.S. Pat. No. 10,654,831 B2, U.S. Appl. No. 16/230,388, Strum, et al., May 19, 2020.
U.S. Pat. No. 10,660,896 B2, U.S. Appl. No. 15/943,278, Strum, et al., May 26, 2020.
U.S. Pat. No. 10,696,682 B2, U.S. Appl. No. 16/226,430, Tavares et al., Jun. 30, 2020.
U.S. Pat. No. 10,709,711 B2, U.S. Appl. No. 16/228,308, Strum, et al., Jul. 14, 2020.
U.S. Pat. No. 10,829,490 B2, U.S. Appl. No. 16/230,396, Strum, et al., Nov. 10, 2020.
US, 2018/0360840 A1, U.S. Appl. No. 16/112,360, Strum, et al., Dec. 20, 2018.
US, 2019/0070185 A1, U.S. Appl. No. 16/178,419, Strum, et al., Mar. 7, 2019.
US, 2019/0135820 A1, U.S. Appl. No. 16/230,308, Smith et al., May 9, 2019.
US, 2019/0151311 A1, U.S. Appl. No. 16/254,364, Strum, et al., May 23, 2019.
US, 2019/0167691 A1, U.S. Appl. No. 16/268,317, Strum, et al., Jun. 6, 2019.
US, 2019/0321370 A1, U.S. Appl. No. 16/432,244, Sorrentino et al., Oct. 24, 2019.
US, 2019/0321332 A1, U.S. Appl. No. 16/460,502, Strum et al., Oct. 24, 2019.
US, 2020/0022983 A1, U.S. Appl. No. 16/572,418, Strum, et al., Jan. 23, 2020.
US, 2020/0123168 A1, U.S. Appl. No. 16/721,631, Smith et al., Apr. 23, 2020.
US, 2020/0216406 A1, U.S. Appl. No. 16/824,290, Strum, et al., Jul. 9, 2020.
US, 2020/0239486 A1, U.S. Appl. No. 16/847,426, Strum, et al., Jul. 30, 2020.
US, 2020/0277300 A1, U.S. Appl. No. 15/931,330, Tavares et al., Sep. 3, 2020.
US, 2020/0283406 A1, U.S. Appl. No. 16/877,249, Strum, et al., Sep. 10, 2020.
US, 2020/0331925 A1, U.S. Appl. No. 16/918,985, Strum, et al., Oct. 22, 2020.
US, 2020/0345742 A1, U.S. Appl. No. 16/886,309, Strum, et al., Nov. 5, 2020.
US, 2020/0345743 A1, U.S. Appl. No. 16/926,035, Strum, et al., Nov. 5, 2020.
U.S. Appl. No. 16/924,033, Beelen et al., filed Jul. 8, 2020.
U.S. Appl. No. 17/067,549, Strum, et al., filed Oct. 9, 2020.
U.S. Appl. No. 17/088,298, Strum, et al., filed Nov. 3, 2020.
Berz et al., Lerociclib (G1T38), an oral cdk4/6 inhibitor, dosed continuously in combination with osimertinib for EGFRmut non-small cell lung cancer: initial phase 1B results. ESMO Congress 2019 Sep. 27-Oct. 1, 2019, Barcelona, Spain (also available at: https://www.g1therapeutics.com/file.cfm/34/docs/le-G1_ESMO2019_Berz.pdf).
Bisi et al., Preclinical Characterization of G1T28: A Novel CDK4/6 Inhibitor for Reduction of Chemotherapy-Induced Myelosuppression, Mol. Cancer Therap. (2016) (15)5: 783-793.
Bisi et al., Preclinical Characterization of G1T38: A novel, potent and selective CDK4/6 inhibitor of cyclin dependent kinases 4/6 for use as an oral neoplastic in patients with CDK4/6 sensitive tumors. Oncotarget, 2017, vol. 8, (No. 26), pp. 42343-42358.
Bonelli M.A. et al., "Combined inhibition of CDK 4/6 and PI3K/AKT/mTOR pathways induces a synergistic anti-tumor effect in malignant pleural mesothelioma cells", Neoplasia, 2017, 19(8), 637-648.
Fry, D. W. et al. "Specific inhibition of cyclin-dependent kinase 4/6 by PD 0332991 and associated antitumor activity in human tumor xenografts" Mol Cancer Ther., Nov. 2004; 3(11): 1427-1438.
Goel S. et al., "Overcoming therapeutic resistance in HER2-positive breast cancers with CDK 4/6 inhibitors", Cancer Cell, 2016, 29, 255-269.
Goel, S. et al., CDK4/6 Inhibition Triggers Anti-Tumour Immunity; Nature. Aug. 24, 2017; 548 (7668): 471-475. doi: 10.1038/nature23465. Epub Aug. 16, 2017.
International Search Report and Written Opinion for PCT/US2018/19291 dated May 30, 2018.
Johnson, N. and G. Shapiro "Cyclin-dependent kinase 4/6 inhibition in cancer therapy" Cell Cycle, Nov. 1, 2012; 11(21): 3913-3918.
Johnson et al., Cyclin-dependent kinases (cdks) and the DNA damage response: rationale for cdk inhibitor-chemotherapy combi-

(56) References Cited

OTHER PUBLICATIONS nations as an anticancer strategy for solid tumors, Expert Opin Ther Targets. Nov. 2010; 14(11): 1199-1212.

Mcinnes, C. "Progress in the evaluation of CDK inhibitors as anti-tumor agents" Drug Discov Today, Oct. 2008; 13(19-20): 875-881.

NCT02779751—A Study of Abemaciclib (LY2835219) in Participants with Non-Small Cell Lung Cancer or Breast Cancer; May 20, 2016.

Roberts et al. "Multiple Roles of Cyclin-Dependent Kinase 4/6 Inhibitors in Cancer Therapy" JNCI, 2012; 104(6):476-487.

Smith B et al., "Single oral dose acute and subacute toxicity of a c-MET tyrosine kinase inhibitor and CDK 4/6 inhibitor combination drug therapy", Am J. Cancer Res., 2018, 8(1), 183-191.

Stice, James P. et al., "CDK4/6 Therapeutic Intervention and viable alternative to taxane in CRPC", Molecular Cancer Research, 2017, 15(6), 660-669, XP55457140.

Tan et al., "Trilaciclib plus chemotherapy versus chemotherapy alone in patients with metastatic triple-negative breast cancer: a multicenter, randomized, open-label, phase 2 trial", Lancet Oncol., 2019, 20, 1587-1601.

Tao Z et al., "Coadministration of trametinib and palbociclib radiosensitizers KRAS-Mutant non-small cell lung cancers in vitro and in vivo", Cancer Therapy, 2016, 22(1), 122-133.

Tate et al., Semi-Mechanistic Pharmacokinetic/Pharmacodynamic Modeling of the Antitumor Activity of LY2835219, a New Cyclin-Dependent Kinase 4/6 Inhibitor, in Mice Bearing Human Tumor Xenografts, Clin Cancer Res (Jul. 15, 2014) 20; 3763.

Weiss et al., "Myelopreservation with the CDK inhibitor trilaciclib in patients with small cell lung cancer receiving first-line chemotherapy: a phase Ib/randomized phase II trial", Annals of Oncology, 2019, 30, 1613-1621.

Wood A.C. et al., "Dual ALK and CDK 4/6 inhibition demonstrates synergy against neuroblastoma", Clin. Cancer Res., 2017, 23(11), 2856-2868.

Yu et al., Resistance to an Irreversible Epidermal Growth Factor Receptor (EGFR) Inhibitor in EGFR-Mutant Lung Cancer Reveals Novel Treatment Strategies. Cancer Res 2007; 67: (21). Nov. 1, 2007.

Zhou J et al., "Palbociclib, a selective CDK 4/6 inhibitor, enhances the effect of selumetinib in RAS-driven non-small cell lung cancer", Cancer Letters, 2017, 408, 130-137.

Zhou et al., "CDK4/6 or MAPK blockade enhances efficacy of EGFR inhibition in oesophageal squamous cell carcinoma." Nature Communications, 2016, 6:13897.

Spring et al., Clinical Management of Potential Toxicities and Drug Interactions Related to Cyclin-Dependent Kinase 4/6 inhibitors in Breast Cancer: Practical Considerations and Recommendations. The Oncologist 2017; 22:1-10.

Chee-Seng Tan et al., "Next generation epidermal growth factor tyrosine kinase inhibitors in epidermal growth factor receptor mutant non-small cell lung cancer", Lung Cancer, Elsevier, 2016, 93, 59-68; Jan. 8, 2016.

Sheelagh et al., "Synergistic combinations between the oral CDK inhibitor, seliciclib, and either EGFR inhibitor or DNA damaging agents in NSCLC", American association for Cancer Research Proceedings of the Annual Meeting, American Association for Cancer Research, 2007, 48, 947; Apr. 1, 2007.

Sorrentino J et al., "Abstract 2824: G1T38, a novel, oral, potent and selective CDK 4/6 inhibitor for the treatment of Rb competent tumors", Cancer Research, 2016, 1-2; Apr. 16, 2016.

U.S. Pat. No. 10,865,210 B2, U.S. Appl. No. 16/230,381, Smith et al., Dec. 15, 2020.

U.S. Pat. No. 10,925,878 B2, U.S. Appl. No. 16/178,419, Strum et al., Feb. 23, 2021.

U.S. Pat. No. 10,927,120 B2, U.S. Appl. No. 16/721,631, Smith et al., Feb. 23, 2021.

U.S. Pat. No. 10,966,984 B2, U.S. Appl. No. 16/112,360, Strum et al., Apr. 6, 2021.

U.S. Pat. No. 10,981,887 B2, U.S. Appl. No. 16/824,290, Strum et al., Apr. 20, 2021.

U.S. Pat. No. 10,988,479 B2, U.S. Appl. No. 17/097,854, Schneider, Apr. 27, 2021.

U.S. Pat. No. 11,040,042 B2, U.S. Appl. No. 16/886,309, Strum et al., Jun. 22, 2021.

US, 2019/0374545 A1, U.S. Appl. No. 16/547,342, Sorrentino, et al., Dec. 12, 2019.

US, 2020/0405721 A1, U.S. Appl. No. 16/924,033, Beelen et al., Dec. 31, 2020.

US, 2021/0030758 A1, U.S. Appl. No. 17/067,549, Strum, et al., Feb. 4, 2021.

US, 2021/0047328 A1, U.S. Appl. No. 17/088,298, Strum, et al., Feb. 18, 2021.

US, 2021/0077498 A1, U.S. Appl. No. 17/102,311, Strum, et al., Mar. 18, 2021.

US, 2021/0122755 A1, U.S. Appl. No. 17/121,392, Smith et al., Apr. 29, 2021.

US, 2021/0171554 A1, U.S. Appl. No. 17/176,962, Strum, et al, Jun. 10, 2021.

US, 2021/0179567 A1, U.S. Appl. No. 17/184,354, Schneider et al., Jun. 17, 2021.

US, 2021/0213022 A1, U.S. Appl. No. 17/181,638, Strum, et al., Jul. 15, 2021.

US, 2021/0267986 A1, U.S. Appl. No. 17/315,011, Sorrentino et al., Sep. 2, 2021.

US, 2021/0299130 A1, U.S. Appl. No. 17/222,873, Strum, et al., Sep. 30, 2021.

US, 2021/0387993 A1, U.S. Appl. No. 17/236,687, Schneider et al., Dec. 16, 2021.

U.S. Appl. No. 17/403,577, Strum et al., filed Aug. 16, 2021.

U.S. Appl. No. 17/554,940, Roberts et al., filed Dec. 17, 2021.

NCT03455829—G1T38, a CDK 4/6 Inhibitor, in Combination With Osimertinib in EGFR-Mutant Non-Small Cell Lung Cancer. Available at https://www.clinicaltrials.gov/ct2/show/NCT03455829?term=lerociclib&draw=2&rank=3. First available on Mar. 7, 2018. Accessed on Feb. 7, 2022.

Beck, Tim N., et al. "EGFR and RB1 as Dual Biomarkers in HPV-Negative Head and Neck Cancer," Companion Diagnostics and Cancer Biomarkers, Molecular Cancer Therapeutics, 15(10) Oct. 2016.

* cited by examiner

TREATMENT OF EGFR-DRIVEN CANCER WITH FEWER SIDE EFFECTS

STATEMENT OF RELATED APPLICATIONS

This application is a continuation of International Patent Application No. PCT/US18/19291, filed Feb. 22, 2018, which claims benefit of U.S. Provisional Application No. 62/462,094, filed Feb. 22, 2017. The entirety of both applications are incorporated herein for all purposes.

FIELD OF THE INVENTION

This invention provides methods of treating epidermal growth factor receptor-mutant (EGFR-mutant) cancers in a patient with acquired or intrinsic resistance to epidermal growth factor receptor-tyrosine kinase inhibitors (EGFR-TKI).

BACKGROUND

The epidermal growth factor receptor (EGFR) is overexpressed, dysregulated, or mutated in many epithelial malignancies, and EGFR activation appears important in tumor growth and progression. Activation of EGFR stimulates tumor growth and progression, including the promotion of proliferation, angiogenesis, invasion, metastasis, and inhibition of apoptosis. Tumors prone to the effects of EGFR dysregulation include bladder cancer, gliomas including glioblastoma, head and neck cancer, breast cancer, cervical cancer, uterine cancer, colon and colorectal cancer, esophageal cancer, non-small cell lung carcinoma (NSCLC), ovarian cancer, pancreatic cancer, and renal cell carcinoma, squamous cell carcinoma, and thyroid cancer.

In recent years, EGFR-mutant NSCLC has emerged as a unique subset in terms of etiopathogenesis and tumor biology. EGFR activity in these cells can be dysregulated by oncogenic mechanisms including increased EGFR gene copy number, EGFR overexpression, and activating gene mutations. This results in autophosphorylation of the cytoplasmic receptor domain and subsequently activates downstream signaling cascades including the mitogen-activated protein kinase (MAPK), mammalian target of rapamycin (mTOR), and Janus kinase-signal transducers and activators of transcription (JAK-STAT) pathways (Ciardiello et al., "EGFR antagonists in cancer treatment." N Eng J Med 2008; 358:1160-1174). These EGFR activated pathways drive tumor growth and replication and may ultimately counteract apoptosis and enhance cellular metabolism, as well as contribute to metastatic spread, angiogenesis, and resistance to anti-neoplastic agents or radiotherapy (Ang et al., "Impact of epidermal growth factor receptor expression on survival and pattern of relapse in patients with advanced head and neck carcinoma." Cancer Res 2002; 62:7350-7356; Milas et al., "Epidermal growth factor receptor and tumor response to radiation: In vivo preclinical studies." Int J Radiat Oncol Biol Phys 2004; 58:966-971).

Because conventional chemotherapy regimens have had limited efficacy, targeted therapies such as those that inhibit the EGFR signaling pathway are being extensively evaluated in patients with EGFR-mutant NSCLC. (Pao et al., Nat Rev Cancer 2010; 10:760-774). First-line therapies incorporating EGFR-TKIs such as gefitinib (IRESSA) and erlotinib (TARCEVA) have shown to be effective in advanced NSCLC harboring recurrent somatic activating mutations occurring in the exons encoding the kinase domain of EGFR, i.e., small multi-nucleotide in-frame deletions in exon 19 (ex19del) and a point mutation in exon 21 leading to substitution of leucine for arginine at position 858 (L858R) (Lynch et al., N Eng J Med 2004; 350:2129-39; Paez et al., Science 2004; 304:1497-500; Pao et al., PNAS 2004; 101:13306-11). These somatic mutations in EGFR lead to constitutive activation of EGFR signaling and oncogenic transformation (Ji et al., Cancer Cell 2006; 9:485-95).

Unfortunately, while a reasonable number of patients with EGFR-mutant NSCLC respond to EGFR-TKI therapy initially, most patients who respond to therapy ultimately develop disease progression after about 9-14 months of treatment due to acquired resistance to the EGFR-TKI (Maemondo et al., N Eng J Med 2010; 362:2380-8). In approximately 60% of these patients, the mechanism of acquired resistance is the development of an additional EGFR mutation, T790M (Yu et al., Clin Cancer Res 2013; 19:2240-7). The T790M substitution leads to an enhanced affinity for ATP, reducing the ability of ATP-competitive reversible EGFR tyrosine kinase inhibitors such as gefitinib and erlotinib to bind to the tyrosine kinase domain of EGFR (Yun et al., PNAS 2008; 105:2070-5). Other mutations leading to EGFR-TKI acquired resistance include MET amplification, HER2 amplification, epithelial-mesenchymal transition (EMT), and transformation of NSCLC to small-cell histology (Takezawa et al., Cancer Discov. 2012; 2(10): 922-933; Uramoto et al., Lung Cancer 2011; 73(3):361-365). Second-generation EGFR-TKIs such as afatinib, neratinib, and dacomitinib are irreversible EGFR-TKIs which have more potent EGFR inhibition than gefitinib and erlotinib. These second-generation EGFR-TKIs, however, are also prone to acquired resistance with the acquisition of T790M being the most prevalent cause (Wu et al., Oncotarget 2016; 7(11):12404-12413).

Third-generation irreversible pyrimidine EGFR-TKIs including osimertinib (TAGRISSO), rociletinib (CO-1686), olmutinib (OLITA; BI 1482694; HM61713), naquotinib (ASP8273), nazartinib (EGF816), and PF-06747775 have emerged to target both EGFR-mutant and EGFR-mutant T790M-positive NSCLC (Cross et al., Cancer Discov. 2014; 4(9):1046-61; Walter et al., Cancer Discov. 2013; 3(12):404-15; Park et al., ASCO Meet Abstr. 2015; 33(15)8084; Wang et al., J. Hemat. & Oncol. 2016; 9:34). In phase I studies to date, treatment with either osimertinib or rociletinib has resulted in a response rate of >50% in EGFR-mutant EGFR-T790M NSCLC patients who have developed resistance to gefitinib or erlotinib (Janne et al., N Eng J Med 2015; 372:1689-99; Sequist et al., N Eng J Med 2015; 372:1700-9). The third-generation EGFR-TKIs, however, are also prone to eventual ineffectiveness through acquired resistance. The most common mutation leading to resistance includes C797 mutations C797S and C797G (Ercan et al., Clin Can Res 2015 21(17)3913-3923). Cysteine 797 is the site of covalent binding for both rociletinib and osimertinib (Zhou et al., Nature 2009; 462:1070-4). Furthermore, in certain patient sub-populations, the T790M mutation renders the tumor resistant to these third-generation EGFR-TKIs, even without the development of C797S mutations. The loss of the T790M mutation in patients on third-generation EGFR-TKIs is associated with a rapid onset of resistance compared to the maintenance of the T790M mutation. (Oxnard et al., J. Thoracic Oncology, November 2017 Vol. 12 (11), Sup. 2, p. S1767-S1768).

Importantly, about 20-30% of patients with EGFR-mutant NSCLC have little or no objective response to first line EGFR-TKI treatment. These patients represent a subgroup that is defined as having intrinsic or primary resistance to EGFR-TKIs. (See Wang et al, Oncotargets and Therapy 2016:9; 3711-3726). EGFR activating mutations associated with EGFR-TKI intrinsic resistance include exon 20 insertions (with the exception of the A763_Y764insFQEA in the C-terminal helix of EGFR). Clinical studies indicate that the majority of patients with an exon 20 insertion do not respond to EGFR-TKI therapy (Naidoo et al., Cancer 2015; 121(18): 3212-3220). In addition, somatic exon 20 insertions in HER2 lead to constitutive phosphorylation and activation of HER2 and EGFR and confer intrinsic resistance (See Wang et al., Cancer Cell 2006; 10(1):25-38). Somatic PIK3CA mutations in the catalyst domain of PIK3CA have been associated with intrinsic resistance (Engelman et al., J. Clin. Invest. 2006; 116(10):2695-2706). Other intrinsic resistance mechanisms include naive T790M mutations, loss of PTEN expression or function, MLH1 V384D polymorphism, de novo presence of MET amplification, KRAS mutations, and a germline deletion polymorphism of BIM, microRNA expression of miR-21, miR-271, and miR-218, HGF expression, and CRIPTO1 expression (see Wang et al. 2016).

A number of strategies have been suggested to combat resistance to EGFR-TKI therapy in NSCLC. For example, combination therapy using an EGFR-TKI and cytotoxic chemotherapy has been studied. However, the results indicate that such a strategy is limited in its effectiveness (See Wang et al. 2016). Other strategies include combining EGFR-TKI and: the EGFR monoclonal antibody cetuximab; the MET inhibitor INC280; the MET inhibitor tivantinib; the dual MET-VEGF inhibitor cabozantinib; the dual inhibitor of PI3K/mTOR NVP-BEZ235; the AKT inhibitor MK2206; the VEGF inhibitor bevacizumab; the PD-1 checkpoint inhibitor nivolumab; the PD-1 inhibitor pembrolizumab; the PPAR-gamma agonist rosiglitazone; and the HDAC inhibitor vorinostat, respectively. Such strategies, however, have been met with mixed or limited results (See Wang et al. 2016).

Liu et al. reported that administration of a cyclin dependent kinase 4/6 inhibitor—PD-0332991 (palbociclib)—in combination with gefitinib in a NSCLC patient that developed EGFR-TKI acquired resistance showed a reduction in brain metastases (Liu et al., Oncotarget 2016, Vol. 7(51); 84951-84964). Liu et al., however, indicate that more studies are needed to determine the efficacy and side effects of PD-0332991 co-administration. WO 2017/037576 describes combining the CDK 4/6 inhibitor ribociclib with the EGFR-TKI erlotinib to treat certain cancers, including NSCLC. Palbociclib (Ibrance) and ribociclib (Kisqali) are also being clinically tested in combination with cetuximab (Erbitux), a monoclonal antibody to EGFR, in the head and neck cancer population.

The use of certain CDK 4/6 inhibitors including palbociclib, ribociclib, and abemaciclib, however, has been associated with severely limiting toxicities. For example, the use of palbociclib (IBRANCE/Pfizer) commonly results in the development of Grade 3/4 neutropenia and leukopenia. Neutropenia was the most frequently reported adverse reaction in Study 1 (PALOMA-2) with an incidence of 80% and Study 2 (PALOMA-3) with an incidence of 83%. A Grade ≥3 decrease in neutrophil counts was reported in 66% of patients in PALOMA-2 and PALOMA-3. The median time to first episode of any grade neutropenia was 15 days and the median duration of Grade ≥3 neutropenia was 7 days. This resulted in 71% of patients requiring a dose interruption, 36% requiring a dose reduction, and 8% leading to complete drug discontinuation (see Finn, Abstract S1-6, SABCS 2012). Additional concerns include potential hepatotoxicity. Increased aspartate aminotransferase (AST) occurred in 48% of patients treated and increased alanine transferase occurred in 40% of patients treated. These side effects may be caused by the undesirable pharmacokinetics of palbociclib, which has a relatively long T½ of roughly 27 hours, resulting in an accumulative concentration build-up of the CDK4/6 inhibitor and a persistent quiescence of hematopoietic stem cell (HPSC) replication. Due to these effects, the approved dosing regimen for palbociclib requires a 7-day holiday after 21-days of once daily dosing, reducing the effectiveness of the anti-neoplastic treatment.

The use of ribociclib (KISQALI/Novartis) is associated numerous adverse reactions including neutropenia (75%), fatigue (37%), diarrhea (35%), alopecia (33%), leukopenia (33%), vomiting (29%), constipation (25%), headache (22%), and back pain (20%). Grade 3/4 decrease in neutrophil count (based on laboratory findings) was reported in 60% of patients receiving ribociclib. KISQALI has been shown to prolong the QT interval in a concentration-dependent manner. In the MONALEESA-2 study, 3.3% of patients treated with ribociclib had at least one average QTcF interval of more than 480 msec after baseline (see Spring, L. M. et al. The Oncologist, 2017, 22:1-10). Hepatic toxicity is also a concern. Grade 3 or 4 increases in ALT (10%) and AST (7%) were reported in the KISQALI treatment arms. Dose reductions due to adverse reactions (ARs) occurred in 45% of patients receiving ribociclib. Permanent discontinuations due to ARs were reported in 7% of patients receiving ribociclib. The most common ARs leading to treatment discontinuation were increased ALT (4%), increased ALT (3%), and vomiting (2%). These side effects may be caused by the undesirable pharmacokinetics of ribociclib, which has a relatively long T½ of roughly 32 hours, resulting in an accumulative concentration build-up of the CDK4/6 inhibitor and a persistent quiescence of HPSC replication. Due to these effects, the approved dosing regimen for ribociclib requires a 7-day holiday after 21-days of once daily dosing, reducing the effectiveness of the anti-neoplastic therapy.

The use of abemaciclib (VERZENIO/Eli Lilly & Co.) is associated with significant adverse reactions and toxicities. Diarrhea and neutropenia were the most common adverse reactions. Diarrhea occurred in 86% of patients receiving VERZENIO plus fulvestrant in MONARCH 2 and 90% of patients receiving VERZENIO alone in MONARCH 1. Grade 3 diarrhea occurred in 13% of patients receiving VERZENIO plus fulvestrant in MONARCH 2 and in 20% of patients receiving VERZENIO alone in MONARCH 1. Neutropenia occurred in 46% of patients receiving VERZENIO plus fulvestrant in MONARCH 2 and 37% of patients receiving VERZENIO alone in MONARCH 1. A Grade ≥3 decrease in neutrophil count (based on laboratory findings) occurred in 32% of patients receiving VERZENIO plus fulvestrant in MONARCH 2 and in 27% of patients receiving abemaciclib in MONARCH 1. Alanine aminotransferase (ALT) increased in 41% of patients and aspartate aminotransferase (AST) increased in 37% of patients. Dose reductions due to an adverse reaction occurred in 43% of patients receiving VERZENIO plus fulvestrant. Dose reductions due to diarrhea of any grade occurred in 19% of patients. Dose reductions due to neutropenia of any grade occurred in 10% of patients. Supportive care was also required. Permanent treatment discontinuation due to an adverse event occurred in 9% of patients. These side effects may be caused by the undesirable pharmacokinetics of abemaciclib.

Because of the toxicities associated with the use of EGFR-TKIs, the addition of a CDK 4/6 inhibitor with significant toxicities raises significant safety concerns due to the potential of an additive toxic side-effect stacking effect.

For example, the use of erlotinib (TARCEVA/Roche) is associated with significant adverse reactions and toxicities. The most frequent (≥30%) adverse reactions in TARCEVA-treated patients were diarrhea, asthenia, rash, cough, dyspnea, and decreased appetite. In TARCEVA-treated patients the median time to onset of rash was 15 days and the median time to onset of diarrhea was 32 days. The most frequent Grade 3-4 adverse reactions in TARCEVA-treated patients were rash and diarrhea. Dose interruptions or reductions due to adverse reactions occurred in 37% of TARCEVA-treated patients, and 14.3% of TARCEVA treated patients discontinued therapy due to adverse reactions. In TARCEVA-treated patients, the most frequently reported adverse reactions leading to dose modification were rash (13%), diarrhea (10%), and asthenia (3.6%). Cases of serious Interstitial lung disease (ILD), including fatal cases, have been reported with TARCEVA treatment. The overall incidence of ILD in approximately 32,000 TARCEVA-treated patients all studies was approximately 1.1%. In patients with ILD, the onset of symptoms was between 5 days to more than 9 months (median 39 days) after initiating TARCEVA therapy. Grade 2 and Grade 3 liver function test abnormalities (including elevated alanine aminotransferase (ALT, aspartate aminotransferase (AST) and bilirubin) were observed in patients receiving TARCEVA.

Use of gefitinib (IRESSA/AstraZeneca) is associated with significant adverse reactions and toxicities. The most frequent reported adverse reactions with IRESSA across NSCLC reported in more than 20% of patients and greater than placebo, were skin reactions (47%) and diarrhea (29%). Additional reported adverse reactions with IRESSA include nausea (18%), asthenia (17%), pyrexia (9%), alopecia (4.7%), hemorrhage (including epistaxis and hematuria) (4.3%), dry mouth (2%), dehydration (1.8%), allergic reactions including angioedema and urticaria (1.1%), elevations in blood creatinine (1.5%), and pancreatitis (0.1%). Interstitial Lung Disease (ILD) or ILD-like reactions (e.g., lung infiltration, pneumonitis, acute respiratory distress syndrome, or pulmonary fibrosis) occurred in 1.3% of 2462 IRESSA patients; of these, 0.7% were Grade ≥3 and 3 cases were fatal. IRESSA has been shown to increase hepatotoxicity. In patients who received IRESSA, 11.4% of patients had increased alanine aminotransferase (ALT), 7.9% of patients had increased aspartate aminotransferase (AST), and 2.7% of patients had increased bilirubin. Grade ≥3 liver test abnormalities occurred in 5.1% ALT, 3.0% AST, and 0.7% bilirubin of patients. The incidence of fatal hepatotoxicity was 0.04%. Grade ≥3 diarrhea occurred in 3% of 2462 IRESSA patients.

Afatinib (GILOTRIF/Boehringer Ingelheim) use is associated with significant adverse events and toxicities. In GILOTRIF-treated patients (n=229) the most common adverse reactions (≥20% all grades & vs pemetrexed/cisplatin-treated patients (n=111)) is diarrhea (96% vs 23%), rash/acneiform dermatitis (90% vs 11%), stomatitis (71% vs 15%), paronychia (58% vs 0%), dry skin (31% vs 2%), and pruritus (21% vs 1%). Other clinically important adverse reactions observed in patients treated with GILOTRIF include: decreased appetite (29%), nausea (25%), and vomiting (23%). Serious adverse reactions were reported in 29% of patients treated with GILOTRIF. The most frequent serious adverse reactions reported in patients treated with GILOTRIF were diarrhea (6.6%), vomiting (4.8%), and dyspnea, fatigue, and hypokalemia (1.7% each). Fatal adverse reactions in GILOTRIF-treated patients included pulmonary toxicity/interstitial lung disease (ILD)-like adverse reactions (1.3%), sepsis (0.43%), and pneumonia (0.43%).

More GILOTRIF-treated patients (2.2%) experienced ventricular dysfunction (defined as diastolic dysfunction, left ventricular dysfunction, or ventricular dilation; all <Grade 3) compared to chemotherapy-treated patients (0.9%). In 3865 patients, 10.1% had liver test abnormalities, of which 0.18% were fatal.

Osimertinib (TAGRISSO/Astra Zeneca) use is associated with significant adverse reactions and toxicities. The most common adverse reactions (≥20%) in patients treated with TAGRISSO are diarrhea (41%), rash (34%), dry skin (23%), nail toxicity (22%), and fatigue (22%). Interstitial Lung Disease (ILD)/Pneumonitis occurred in 3.5% and was fatal in 0.6% of 833 TAGRISSO-treated patients. Heart rate-corrected QT (QTc) interval prolongation occurred in TAGRISSO-treated patients. Of the 833 TAGRISSO-treated patients, 0.7% of patients were found to have a QTc >500 msec, and 2.9% of patients had an increase from baseline QTc >60 msec. No QTc-related arrhythmias were reported. Cardiomyopathy occurred in 1.9% and was fatal in 0.1% of 833 TAGRISSO-treated patients. Left Ventricular Ejection Fraction (LVEF) decline ≥10% and a drop to <50% occurred in 4% of 655 TAGRISSO-treated patients. Keratitis was reported in 0.7% of 833 TAGRISSO-treated patients in clinical trials. Significantly less frequent, but potentially more severe osimertinib-related AEs include pneumonitis/interstitial lung disease, QTc prolongation, cardiomyopathy, and keratitis. Neutropenia, the vast majority Grade 1 or 2, has also been observed with osimertinib therapy, with up to 2.2% of patients experiencing Grade 3 neutropenia.

Both intrinsic and acquired drug resistance remains a major problem in treating EGFR-mutant NSCLC. It is an object of the present invention to provide methods and treatments which effectively treat EGFR-mutant NSCLC that is intrinsically resistant to EGFR-TKI therapy without toxic side-effect stacking. In addition, it is an object of the present invention to safely and effectively reduce or delay the development of EGFR-TKI required resistance in EGFR-mutant NSCLC with a therapeutic regime capable of long-term administration.

SUMMARY OF INVENTION

The present invention provides advantageous methods and compositions to treat a cancer patient with a driving EGFR-mutation (EGFR-mutant cancer), which includes administering an effective amount of a compound selected from the group consisting of:

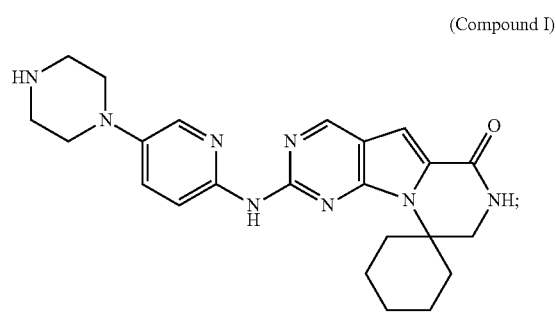

(Compound I)

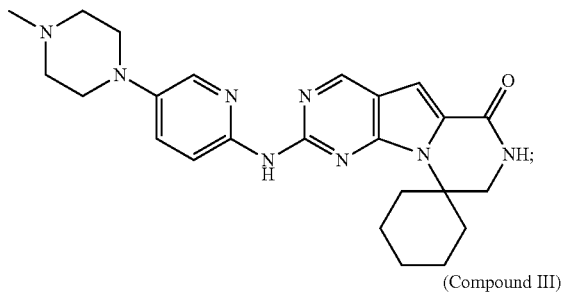
(Compound II)

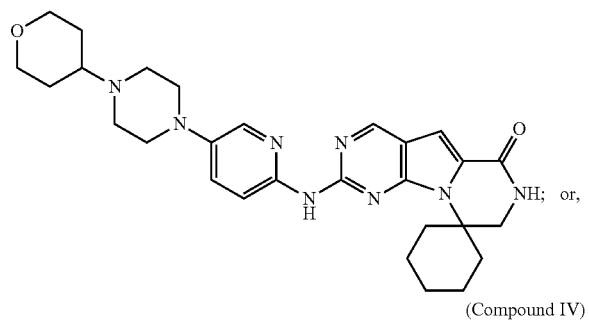
(Compound III)

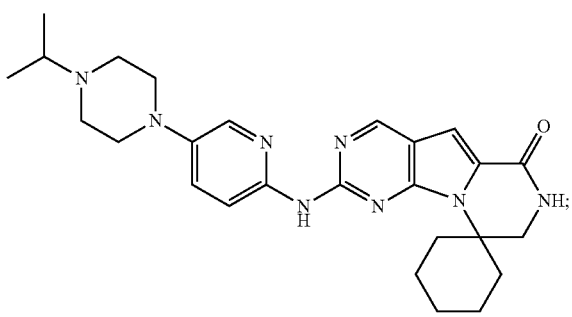
(Compound IV)

or a pharmaceutically acceptable composition, salt, isotopic analog, or prodrug thereof, in combination or alternation with an epidermal growth factor-tyrosine kinase inhibitor (EGFR-TKI) in a manner that minimizes potentially treatment-stopping side effects or otherwise challenging side effects for the patient. Compounds I-IV are described in, for example, U.S. Pat. No. 9,527,857. For illustrative and exemplary purposes, Compound IV is used throughout the specification as representative of the above described CDK 4/6 inhibitors.

It is known that while EGFR-TKIs are beneficial treatments for suitable cancer patients in need thereof, they cause significant side effects that can be difficult to manage, including gastrointestinal problems such as diarrhea, liver toxicities, and, in some cases, hematological deficiencies and cardiologic complications such as Qt elongation. This is exacerbated during combination therapy, because the already difficult EGFR-TKI side effects are then stacked with the potential side effects of the second anti-neoplastic therapy, which can cause either additive or even synergistic complications—so called side-effect stacking.

The CDK 4/6 inhibitors of Formulas I-IV above can be administered in combination with an EGFR-TKI in a manner that allows daily treatment of the patient without a drug holiday or without serious side-effect stacking problems, such as, for example severe dose limiting gastrointestinal issues, for example dose limiting Grade 3 or greater diarrhea or Grade 4 or greater neutropenia as averaged over the patient population. The CDK 4/6 inhibitors described herein for use in combination with an EGFR-TKI are short-acting, having short half-lives (less than about 16 hours) and non-limiting side-effects, thus allowing their inclusion in a long-term treatment regime without the need for treatment holidays. Furthermore, by using these particular CDK 4/6 inhibitors, therapy-limiting side effects such as neutropenia and gastrointestinal complications associated with other CDK4/6 inhibitors are avoided, and potential treatment limiting side-effect stacking associated with combining a CDK 4/6 inhibitor with an EGFR-TKI in a combination treatment can be significantly reduced. The CDK 4/6 inhibitors described herein are particularly useful in therapeutic regimens requiring long-term treatment, as required for EGFR-TKI treatment in, for example NSCLC, while minimizing the effect of CDK4/6 inhibitory toxicity on CDK4/6 replication dependent healthy cells, such as hematopoietic stem cells and hematopoietic progenitor cells (together referred to as HSPCs), and allow for continuous, daily dosing. Based on extensive nonclinical data and clinical data to date with, for example Compound IV, none of the more severe EGFR-TKI-related AEs have been observed with Compound IV to date (See Example 6 below), unlike other CDK 4/6 inhibitors.

Cancers with dysregulated EGFR that can be treated using the methods described herein include bladder cancer, a glioma including glioblastoma, a head and neck cancer, a breast cancer, a cervical cancer, a uterine cancer, a colon and/or colorectal cancer, a gastroesophageal cancer, a non-small cell lung carcinoma (NSCLC), a prostate cancer, an ovarian cancer, a pancreatic cancer, a renal cell carcinoma, a squamous cell carcinoma, or a thyroid cancer.

The EGFR-TKI for use in the present invention in combination with the CDK 4/6 inhibitors described herein can be selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EA1045, tarloxotinib (TH-4000; PR-610), PF-06459988 (Pfizer), tesevatinib (XL647; EXEL-7647; KD-019), transtinib, WZ-3146, WZ8040, CNX-2006, lapatinib (Tykerb; GlaxoSmithKline), brigatinib (Alunbrig; Ariad Pharmaceuticals), Compound V described herein, Compound VI described herein, Compound VII described herein, sapitinib, CUDC-101, PD153035, pelitinib, AEE788 (NVP-AEE788), AST-1306, AZ5104, lifirafenib (BGB-283), canertinib, CL-387785 (EKI-785), norcantharadin, vandetanib (Caprelsa), and dacomitinib (PF-00299804; Pfizer), or a combination thereof.

In one embodiment, a CDK 4/6 inhibitor selected from Compounds I-IV is administered in a solid dosage form, for example, but not limited to, a pill, tablet, or gel cap. In another embodiment, a CDK 4/6 inhibitor selected from Compounds I-IV and a EGFR-TKI are administered together in one solid dosage form. In another embodiment, a CDK 4/6 inhibitor selected from Compounds I-IV and a EGFR-TKI are provided in two separate dosage forms but given in a concerted dosage regime. In another embodiment, one or both of the CDK 4/6 inhibitor and EGFR-TKI are administered in a manner wherein at least one is provided parenterally, for example by intravenous delivery. In generally a CDK 4/6 inhibitor selected from Compounds I-IV and a EGFR-TKI are administered using either combination or alteration dosage forms in such a manner that they are present in the plasma of a patient at an effective $C_{trough}$ at the same time.

In a particular aspect, the present invention provides methods for treating a patient with EGFR-mutant cancer that is intrinsically resistant to EGFR-TKI treatment or has developed acquired resistance to an EGFR-TKI treatment by administering to the patient an effective amount of a selective CDK 4/6 inhibitor described herein in combination with an effective amount of an EGFR-TKI in a continuous treatment regime without treatment limiting side-effects. It particular, it has surprisingly been discovered that the use of the short-acting selective CDK 4/6 inhibitors described herein in combination with an EGFR-TKI is efficacious in sensitizing intrinsically resistant EGFR-mutant cancer to the inhibitory effects of the EGFR-TKI. Furthermore, it has been discovered that the administration of a CDK 4/6 inhibitor described herein in combination with an EGFR-TKI delays the onset of resistance to the administered EGFR-TKI. Finally, it has been discovered that incorporating a CDK4/6 inhibitor described herein in combination with an EGFR-TKI—wherein the EGFR-mutant cancer has previously acquired resistance to the EGFR-TKI—reestablishes the sensitivity of the EGFR-mutant cancer to the inhibitory effects of the EGFR-TKI. Accordingly, the methods described herein can drastically expand the population of EGFR-mutant cancer patients responsive to initial EGFR-TKI inhibition and extend the efficacy of current EGFR-TKI treatments against EGFR-mutant cancers by both delaying acquired resistance and re-sensitizing previously resistant tumors to the inhibitory effects of the EGFR-TKI.

In one aspect of the invention, provided herein is a method of treating a patient with an EGFR-mutant cancer by administering a therapeutically effective amount of a selective CDK 4/6 inhibitor described herein in combination with an effective amount of an EGFR-TKI, wherein the patient is EGFR-TKI treatment naïve. In one embodiment, the selective CDK 4/6 inhibitor is Compound IV. In one embodiment, the EGFR-TKI is selected from erlotinib, gefitinib, afatinib, lapatinib, brigatinib, and osimertinib. In one embodiment, the EGFR-TKI is osimertinib. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect of the invention, provided herein is a method of treating a patient with an EGFR-mutant cancer by administering a therapeutically effective amount of a selective CDK 4/6 inhibitor described herein in combination with an effective amount of an EGFR-TKI, wherein the patient is EGFR-TKI treatment naïve and the cancer harbors an EGFR mutation that renders it resistant to EGFR-TKI treatment. In one embodiment, the cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer. In one embodiment, the EGFR-mutant cancer harbors an EGFR exon 20 insertion mutation. In one embodiment, the exon 20 insertion occurs between amino acids 767 to 774. In one embodiment, the exon 20 insertion is D770_N771insNPG. In one embodiment, the EGFR mutation is a G719X or L861X mutation, wherein X represents a different amino acid, for example but not limited to alanine, cysteine, or serine. In one embodiment, the EGFR mutation is selected from V843I, L747S, D761Y, V769M, T854A, and A871E. In one embodiment, the selective CDK 4/6 inhibitor administered is Compound IV. In one embodiment, the EGFR-TKI is selected from erlotinib, gefitinib, afatinib, lapatinib, brigatinib, and osimertinib. In one embodiment, the EGFR-TKI is osimertinib.

In one alternative aspect of the invention, provided herein is a method of treating a patient with an EGFR-mutant cancer by administering a therapeutically effective amount of a selective CDK 4/6 inhibitor described herein in combination with an effective amount of the EGFR-TKI osimertinib, wherein the patient is EGFR-TKI treatment naïve and the EGFR-mutant cancer harbors a T790M EGFR mutation. In one embodiment, the selective CDK 4/6 inhibitor administered is Compound IV. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect of the invention, provided herein is a method of treating a patient with an EGFR-mutant cancer by administering a therapeutically effective amount of a selective CDK 4/6 inhibitor described herein in combination with an effective amount of an EGFR-TKI, wherein the patient is EGFR-TKI treatment naïve and the cancer harbors a non-EGFR mutation that renders it resistant to EGFR-TKI treatment. In one embodiment, the non-EGFR mutation is selected from: a BRAF mutation; a PIK3CA mutation; a MAPK1 amplification; a MET amplification; a HER2 amplification; an increased expression in KDM5, FGF2, FGFR1, AXL, ROR1, Notch-1; an increased activation in NFκB, Wnt-tnkyrase-β-catenin, JAK2, or VEGFR; up-regulation of ADAM17; down-regulation of DAPK or NF-1; loss of expression of IGF binding proteins; loss of PTEN expression or function; MLH1 V384D polymorphism; a KRAS mutation; germline deletion polymorphism of BIM; microRNA expression of miR-21, miR-271, and miR-218; increased HGF expression; CRIPTO1 expression; and SCLC transformation. In one embodiment, the selective CDK 4/6 inhibitor administered is Compound IV. In one embodiment, the EGFR-TKI is selected from erlotinib, gefitinib, afatinib, lapatinib, brigatinib, and osimertinib. In one embodiment, the EGFR-TKI is osimertinib. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect, provided herein is a method of treating a patient with an EGFR-mutant cancer which includes:

a) administering to the patient an EGFR-TKI;

b) monitoring the patient's EGFR-mutational status; and, c) administering to the patient a selective CDK 4/6 inhibitor described herein in combination with the EGFR-TKI upon the detection of an EGFR mutation or non-EGFR mutation that confers resistance upon the cancer to the inhibitory effects of the EGFR-TKI. In one embodiment, the selective CDK 4/6 inhibitor administered is Compound IV. In one embodiment, the EGFR-TKI is selected from erlotinib, gefitinib, afatinib, lapatinib, brigatinib, and osimertinib. In one embodiment, the EGFR-TKI is osimertinib. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect, provided herein is a method of treating a patient with an EGFR-mutant NSCLC which includes:

a) administering to the patient EGFR-TKI osimertinib;
b) monitoring the patient's NSCLC EGFR-mutational status; and,
c) administering to the patient a selective CDK 4/6 inhibitor described herein in combination with osimertinib upon the detection of an EGFR mutation or non-EGFR mutation that confers resistance upon the NSCLC to the inhibitory effects of osimertinib. In one embodiment, the selective CDK 4/6 inhibitor administered is Compound IV. In one embodiment, the mutation is an EGFR C797 mutation, for example C797S or C797G, an EGFR G796D mutation, an EGFR L718V mutation, or the loss of an EGFR T790M mutation. In one embodiment, the non-EGFR mutation is MET amplification or SCLC transformation. In one embodiment, the non-EGFR-mutation is a BRAF, a PIK3CA mutation, a KRAS mutation, a CCDC6-RET fusion, or a FGFR3-TACC fusion. In one embodiment, the BRAF mutation is V600E. In one embodiment, the KRAS mutation is Q61K. In one embodiment, the PIK3CA mutation is E545K, R88Q, or N345K.

In one alternative aspect, provided herein is a method of treating a patient with an EGFR-mutant cancer which includes:
a) administering to the patient an EGFR-TKI;
b) monitoring the patient's cancer's response to the EGFR-TKI;
c) administering to the patient a selective CDK 4/6 inhibitor described herein in combination with the EGFR-TKI upon the detection of the patient's cancer becoming non-responsive to the EGFR-TKI. In one embodiment, the selective CDK 4/6 inhibitor administered is Compound IV. In one embodiment, the EGFR-TKI is selected from erlotinib, gefitinib, afatinib, lapatinib, brigatinib, and osimertinib. In one embodiment, the EGFR-TKI is osimertinib. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer. In one embodiment, the non-responsiveness is disease progression.

In one alternative aspect, provided herein is a method of treating a patient with an EGFR-mutant NSCLC which includes:
a) administering to the patient the EGFR-TKI osimertinib;
b) monitoring the patient's NSCLC response to osimertinib;
c) administering to the patient a selective CDK 4/6 inhibitor described herein in combination with osimertinib upon the detection of the patient's NSCLC becoming non-responsive to osimertinib. In one embodiment, the selective CDK 4/6 inhibitor administered is Compound IV. In one embodiment, the non-responsiveness is NSCLC disease progression.

In one alternative aspect of the invention, provided herein is a method of treating a patient with an EGFR-mutant cancer by administering a therapeutically effective amount of a selective CDK4/6 inhibitor described herein in combination with an EGFR-TKI in a patient having an EGFR-mutant cancer harboring a mutation that confers acquired resistance to an EGFR-TKI, wherein the patient has previously received EGFR-TKI therapy. In one embodiment, the mutation is selected from an EGFR T790M substitution, an EGFR T854A substitution, an EGFR D761Y substitution, and an EGFR L747S substitution. In one embodiment, the patient has previously been administered an EGFR-TKI selected from erlotinib, gefitinib, afatinib, neratinib, brigatinib, lapatinib, and dacomitinib, wherein the EGFR-mutant cancer has acquired resistance to the inhibitory effects of erlotinib, gefitinib, afatinib, neratinib, lapatinib, brigatinib, or dacomitinib. In one embodiment, the EGFR-TKI administered in combination with the CDK4/6 inhibitor is osimertinib, rociletinib, olmutinib, naquotinib, nazartinib, PF-06747775, icotinib, avitinib, EA1045, tarloxotinib, PF-06459988, tesevatinib, transtinib, WZ-3146, WZ8040, or CNX-2006. In one embodiment, the CDK4/6 administered is Compound IV. In one embodiment, the EGFR-TKI administered is osimertinib. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect of the invention, provided herein is a method of treating a patient with an EGFR-mutant cancer which has acquired resistance to the inhibitory effects of an EGFR-TKI by administering a therapeutically effective amount of a CDK4/6 inhibitor described herein in combination with the same EGFR-TKI, wherein the administration of the CDK4/6 inhibitor acts to re-sensitize the cancer to the previously administered EGFR-TKI. In one embodiment, the EGFR-TKI administered is afatinib. In one embodiment, the EGFR-TKI administered is erlotinib. In one embodiment, the EGFR-TKI administered is gefitinib. In one embodiment, the EGFR-TKI administered is neratinib. In one embodiment, the EGFR-TKI administered is dacomitinib. In one embodiment, the EGFR-TKI administered is osimertinib. In one embodiment, the EGFR-TKI administered is brigatinib. In one embodiment, the EGFR-TKI administered is lapatinib. In one embodiment, the CDK4/6 inhibitor administered is Compound IV. In one embodiment, the EGFR-TKI is osimertinib. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect of the invention, provided herein is a method of treating a patient with an EGFR-mutant NSCLC by administering a therapeutically effective amount of a CDK4/6 inhibitor described herein in combination with an EGFR-TKI to a patient having an EGFR-mutant NSCLC harboring an EGFR T790M/C797S or T790M/C797G mutation, wherein the EGFR-TKI administered is osimertinib. In one embodiment, the CDK4/6 inhibitor is Compound IV.

The administration regime for use in the present invention may include daily dosing of both the EGFR-TKI and the CDK 4/6 inhibitor. For example, the EGFR-TKI may be administered at least once a day with the CDK 4/6 inhibitor. Alternatively, the EGFR-TKI inhibitor may be administered once a day and the CDK 4/6 inhibitor dosed at least once a day, for example once a day, twice a day, or three times a day. Because the CDK 4/6 inhibitors described herein are highly tolerable, the therapeutic regime can be dosed continuously without the need for a drug holiday, further extending the combinations beneficial effects. Accordingly, provided herein is a method of treatment by administering a CDK 4/6 inhibitor described herein in combination with an EGFR-TKI, wherein the combination is administered continuously, for example at least 28 days, at least 35 days, at least 56 days, at least 70 days, at least 102 days, at least 204 days, or more, without the need for a scheduled drug holiday.

In one alternative aspect of the present invention, provided herein is a pharmaceutically acceptable composition comprising a CDK4/6 inhibitor selected from Compound I, Compound II, Compound III, or Compound IV, or its pharmaceutically acceptable salt, and an EGFR-TKI selected from erlotinib, gefitinib, afatinib, rociletinib, osimertinib, olmutinib, naquotinib, nazartinib, PF-06747775, icotinib, neratinib, avitinib, EAI045, tarloxotinib, PF-06459988, tesevatinib, transtinib, WZ-3146, WZ8040, CNX-2006, lapatinib, brigatinib, Compound V described herein, Compound VI described herein, Compound VII described herein, sapitinib, CUDC-101, PD153035, pelitinib, AEE788, AST-1306, AZ5104, lifirafenib, canertinib, CL-387785, norcantharadin, vandetanib, and dacomitinib. In one embodiment, the CDK4/6 inhibitor is Compound IV. In one embodiment, the EGFR-TKI is osimertinib.

In one alternative aspect of the present invention, provided herein is a pharmaceutically acceptable composition as described herein, comprising a CDK4/6 inhibitor selected from Compound I, Compound II, Compound III, and Compound IV, or its pharmaceutically acceptable salt, and an EGFR-TKI selected from erlotinib, gefitinib, afatinib, rociletinib, osimertinib, olmutinib, naquotinib, nazartinib, PF-06747775, icotinib, neratinib, avitinib, EAI045, tarloxotinib, PF-06459988, tesevatinib, transtinib, WZ-3146, WZ8040, CNX-2006, lapatinib, brigatinib, Compound V described herein, Compound VI described herein, Compound VII described herein, sapitinib, CUDC-101, PD153035, pelitinib, AEE788, AST-1306, AZ5104, lifirafenib, canertinib, CL-387785, norcantharadin, vandetanib, and dacomitinib, optionally in one or more pharmaceutically acceptable carriers that is useful in the treatment or prevention of an EGFR-mutant NSCLC. In one embodiment, the CDK4/6 inhibitor is Compound IV. In one embodiment, the EGFR-TKI is osimertinib.

In one alternative aspect of the present invention, provided herein is the use of a pharmaceutically acceptable composition as described herein, in the manufacture of a medicament(s) for the treatment or prevention of an EGFR-mutant NSCLC in a patient.

In one alternative aspect of the present invention, provided herein is a method for manufacturing a medicament for the therapeutic use to treat or prevent a EGFR-mutant NSCLC in a patient, for example a human, characterized in that a pharmaceutically acceptable composition as described herein, is used in the manufacture of the medicament(s).

A process for the preparation of a therapeutic product that contain an effective amount of a pharmaceutically acceptable composition as described herein, comprising a CDK4/6 inhibitor selected from Compound I, Compound II, Compound III, and Compound IV, or its pharmaceutically acceptable salt, and an EGFR-TKI selected from erlotinib, gefitinib, afatinib, rociletinib, osimertinib, olmutinib, naquotinib, nazartinib, PF-06747775, icotinib, neratinib, avitinib, EAI045, tarloxotinib, PF-06459988, tesevatinib, transtinib, WZ-3146, WZ8040, CNX-2006, lapatinib, brigatinib, Compound V described herein, Compound VI described herein, Compound VII described herein, sapitinib, CUDC-101, PD153035, pelitinib, AEE788, AST-1306, AZ5104, lifirafenib, canertinib, CL-387785, norcantharadin, vandetanib, and dacomitinib.

In the present invention, the term EGFR-TKI does not include an antibody to EGFR unless specifically identified. In general, the present invention is directed to a method of using two small molecule drugs, a CDK 4/6 inhibitor (Compounds I-IV) and a EGFR-TKI in concerted therapy in a manner that does not cause dose limiting toxicities, for example, but not limited to, a scheduled dose holiday. In another embodiment, the method of treating a patient for an EGFR-mutant cancer does not lead to severe treatment limiting effects, for example Grade 3 or greater diarrhea or Grade 4 or greater neutropenia averaged over the treated patient population. In one embodiment, the CDK 4/6 inhibitor in combination with EGFR-TKI treatment regime does not require a scheduled holiday. In one embodiment, the CDK 4/6 inhibitor in combination with EGFR-TKI treatment regime does not cause Grade III or greater neutropenia as averaged across the patient population receiving the treatment. In one embodiment, the CDK 4/6 inhibitor in combination with EGFR-TKI treatment regime does not cause Grade 4 or greater neutropenia as averaged across the patient population receiving the treatment. In one embodiment, the CDK 4/6 inhibitor in combination with EGFR-TKI treatment regime does not cause Grade 3 or greater diarrhea as averaged across the patient population receiving the treatment. In one embodiment, the CDK 4/6 inhibitor in combination with EGFR-TKI treatment regime does not cause Grade 4 diarrhea as averaged across the patient population receiving the treatment.

In another embodiment, a method of treating a patient with an EGFR-mutant cancer is provided wherein a CDK 4/6 inhibitor described herein is administered in combination with a covalently binding EGFR-TKI.

In another embodiment, a method for treating a patient with an EGFR-mutant cancer is provided wherein a CDK 4/6 inhibitor described herein is administered in combination with an EGFR-TKI, wherein the dosing regime does not include administering a third anti-neoplastic agent including, for example, another kinase inhibitor. In another embodiment, a method for treating a patient with an EGFR-mutant cancer is provided wherein a CDK 4/6 inhibitor described herein is administered in combination with an EGFR-TKI, wherein the dosing regime does not include administering a checkpoint inhibitor.

In another embodiment, a method for treating a patient with an EGFR-mutant cancer is provided wherein a CDK 4/6 inhibitor described herein is administered in combination with an EGFR-TKI, wherein the cancer is bladder cancer, a glioma including glioblastoma, a head and neck cancer, a breast cancer, a cervical cancer, a uterine cancer, a colon and/or colorectal cancer, a gastroesophageal cancer, a non-small cell lung carcinoma (NSCLC), a prostate cancer, an ovarian cancer, a pancreatic cancer, a renal cell carcinoma, a squamous cell carcinoma, or a thyroid cancer.

DETAILED DESCRIPTION

Terminology

Figure 1:
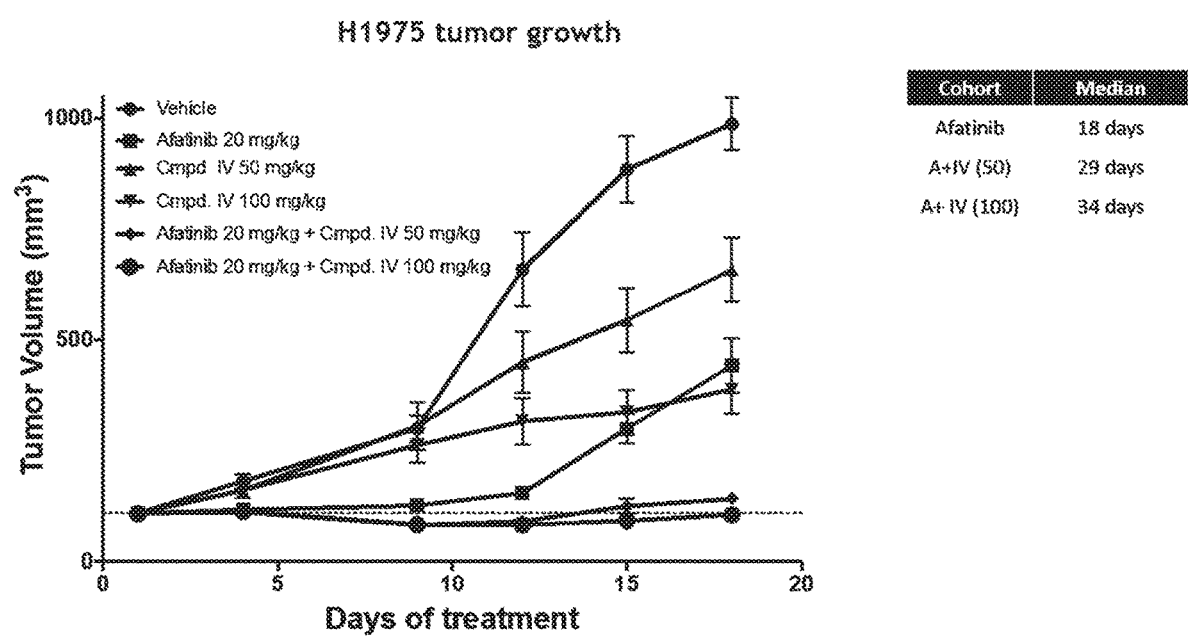
FIG. 1 is a graph showing the combination of a CDK4/6 inhibitor (Compound IV) in combination with a EGFR-TKI (afatinib) increases EGFR-TKI efficacy and extends time to resistance in EGFRL858R/T790M NSCLC model (H1975) compared to EGFR-TKI alone as described in Example 1. The x-axis is days of treatment measured in time and the y-axis is tumor volume measured in $mm^3$.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

"Acquired resistance," as used herein, refers to a condition wherein an EGFR-mutant cancer that was sensitive to the inhibitory effects of at least one EGFR-TKI, becomes non-responsive or less-responsive over time to the effects of that EGFR-TKI. Without wishing to be bound by any one theory, it is believed that acquired resistance to EGFR-TKIs in EGFR-mutant cancers occurs due to one or more additional mutations to EGFR or non-EGFR genetic alterations in bypass signaling that develops after the onset of an EGFR-TKI treatment regimen. For example, non-limiting exemplary acquired resistance EGFR-mutants in NSCLCs include, but are not limited to, EGFR T790M substitutions, C797S substitutions, and C797G substitutions. Non-limiting examples of non-EGFR genetic alterations in bypass signaling include, but are not limited to, Her2 amplification or mutation, Met amplification, HGF overexpression, IGF-1R activation, PTEN loss of function mutations, BIM mutations, CRIPTO 1 expression, and/or P13k activation.

"Intrinsic resistance," also known as primary resistance, as used herein, refers to a condition wherein a cancer with a EGFR-mutation is not response to the inhibitory effects of initial EGFR-TKI treatment. EGFR activating mutations associated with EGFR-TKI intrinsic resistance include, but are not limited to, exon 20 insertions, somatic PIK3CA mutations in the catalyst domain of PIK3CA, naive T790M mutations, loss of PTEN expression or function, MLH1 V384D polymorphism, de novo presence of MET amplification, KRAS mutations, and a germline deletion polymorphism of BIM, microRNA expression of miR-21, miR-271, and miR-218, high HGF expression, and CRIPTO1 expression.

The patient treated is typically a human patient, although it is to be understood the methods described herein are effective with respect to other animals, such as mammals. More particularly, the term patient can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

Compounds are described using standard nomenclature. Unless defined otherwise, all technical and scientific terms used herein have the same meaning as is commonly understood by one of skill in the art to which this invention belongs.

The compound of the present invention may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

Throughout the specification and claims, a given chemical formula or name shall encompass all optical and stereoisomers, as well as racemic mixtures where such isomers and mixtures exist, unless otherwise noted.

EGFR-Mutant Cancers

In general, provided herein are methods for treating a patient with an EGFR-mutant cancer wherein a CDK 4/6 inhibitor described herein is administered in combination with an EGFR-TKI. Tumors prone to the effects of EGFR dysregulation include bladder cancer, gliomas including glioblastoma, head and neck cancer, breast cancer, cervical cancer, uterine cancer, colon and colorectal cancer, gastroesophageal cancer, non-small cell lung carcinoma (NSCLC), prostate cancer, ovarian cancer, pancreatic cancer, renal cell carcinoma, squamous cell carcinoma, and thyroid cancer, and are targets of the methods described herein.

In one embodiment, the EGFR-mutant cancer treated is breast cancer. The breast cancer can be estrogen receptor positive breast cancer. In one embodiment, the cancer is estrogen-receptor positive, HER2-negative advanced breast cancer. Alternatively, the cancer can be estrogen receptor-negative breast cancer. The cancer can be late-line metastatic breast cancer. The cancer can be luminal A breast cancer. The cancer can be luminal B breast cancer. The cancer can be Her2-negative breast cancer or HER2-positive breast cancer. In one embodiment, the cancer can be male breast cancer. In one embodiment, the cancer is progesterone receptor-negative breast cancer. The cancer can be progesterone receptor-positive breast cancer. The cancer can be recurrent breast cancer. In one embodiment, the cancer is stage IV breast cancer. In one embodiment, the cancer is advanced HER2-positive breast cancer. In one embodiment, the cancer is retinoblastoma positive breast cancer. In one embodiment, the estrogen receptor positive breast cancer is resistant to endocrine therapy. In one embodiment, the estrogen receptor positive breast cancer is resistant to tamoxifen.

In one embodiment, the cancer treated is an EGFR-mutant NSCLC. Non-small cell lung cancer (NSCLC) is not a singular entity but multiple pathologies with unique molecular signatures. The main subtypes of NSCLC are pulmonary adenocarcinoma, squamous cell carcinoma (SCC), and large cell carcinoma. NSCLC tumors are typically screened with predictive and/or prognostic biomarkers that help to predict sensitivity to targeted therapy and estimate prognosis respectively.

One predictive biomarker in NSCLC is epidermal growth factor receptor (EGFR)-mutation status. The epidermal growth factor receptor (EGFR or ErbB1 or HER1) belongs to a family of receptor tyrosine kinases that can trigger a vast array of signaling pathways leading to cell growth, proliferation, and survival. These pathways include the RAS-RAF-MEK-ERK or MAPK pathway and the PI3K-AKT-mTOR pathways (see Chan et al., Transl Lung Cancer Res 2015; 4(1):36-54). There are three main mechanisms leading to EGFR activation: increased expression of EGFR on malignant cells; enhanced ligand production by malignant cells; and activating mutations of EGFR within malignant cells. Activating mutations are the primary target of EGFR-TKIs.

The two most common EGFR activating mutations in NSCLC are exon 19 deletions (60%) and L858R missense substitutions at positions 858 (35%) where leucine is replaced by arginine resulting in constitutive activation of the receptor without ligand binding (Yarden et al., Nat Rev Mol Cell Biol 2001; 2:127-37; Jackman et al., Clin Cancer res 2006; 12:3908-14; Rosell et al., N Engl J Med 2009; 361:958-67). Additional mutations have been shown to occur at L861Q, wherein leucine is replaced by glutamine. Further EGFR mutations in NSCLC providing EGFR-TKI sensitivity include G719 mutations in exon 18, V765A, T783A, V774A, and S784P mutations in exon 20 (Stewart et al., Transl Lung Can Res 2015; 4(1):67-81).

The development of acquired resistance is common in EGFR-mutant NSCLC exposed to EGFR-TKIs. Acquired resistance occurs either through secondary EGFR mutations or activation of EGFR-independent pathways. The most common acquired resistance mutation is the acquisition of a mutation in exon 20 of EGFR, encoding T790M, wherein threonine is replaced by methionine, altering the configuration of the kinase domain and enhancing its affinity over wild-type for ATP, with corresponding decreased affinity for first-generation reversible TKIs (Yun et al., PNAS 2008; 105; 2070-5). Additional secondary mutations resulting in acquired resistance to EGFR-TKIs have been reported, including T854A, D761Y, and L747S (Balek et al, Clin Cancer Res 2006; 12:6494-501; Bean et al., Clin Cancer Res 2008; 14:7519-25; Costa et al., PLoS Med 2007; 4:1669-79).

Acquired resistance also develops to EGFR-TKIs directed to EGFR-mutant NSCLC having T790M substitutions that have progressed following treatment with EGFR-TKIs. For example, the acquired C797S and C797G mutations have been identified as a mechanism of resistance to osimertinib, a third-generation irreversible EGFR-TKIs that targets T790M mutant NSCLC. The primary mutations associated with acquired resistance to these T790M directed EGFR-TKIs are Cys797 mutations, including C797S and C797G. Recently, a fourth-generation EGFR-TKI (EAI045) has been developed targeting the C797G and C797S mutation.

Genetic alternations in genes other than EGFR and its associated ErbB family members can occur with activating EGFR mutations and may be responsible for the decreased sensitivity of EGFR-mutant cancers to EGFR-TKI treatment. These alterations include EGFR signal-related and non-EGFR signal related mutations. Non-EGFR mutations include Her2 amplification and/or mutations, for example, somatic exon 20 insertions which lead to constitutive phosphorylation and activation of Her2 and confer resistance to EGFR-TKIs (see Wang et al., Cancer Cell. 2006; 10(1):25-38, incorporated herein by reference). Somatic PIK3CA mutations in the catalytic domain of PIK3CA have been identified in NSCLC tumors after TKI treatment, which is one mechanism related to acquired resistance to EGFR-TKIs through the activation of PI3K (see Sequist et al., Sci Transl Med. 2011; 3(75):75ra26, incorporated herein by reference). PTEN mutations, for example PTEN loss of function mutations or reduced PTEN expression levels, have also been implicated in EGFR-TKI acquired resistance (see Bidkhori et al., PLoS One. 2012; 7(10):e48004, incorporated herein by reference). MET overexpression, phosphorylation, and activation is associated with poor response to EGFR-TKI treatment regardless of EGFR status (see Benedettini et al., Am J Pathol. 2010; 177(1):415-423, incorporated herein by reference). As a ligand of the MET receptor, HGF can confer resistance on NSCLC cells harboring activating EGFR mutations by phosphorylation of MET and activation of the PI3K/Akt pathway (see Gusenbauer et al., Oncogene. 2013; 32(33):3846-3856, incorporated herein by reference). High HGF expression might be more common than other mutations in tumors with primary resistance and may promote intrinsic resistance to EGFR TKIs by activating the MET signaling pathway (see Yano et al., J Thorac Oncol. 2011; 6(12):2011-2017, incorporated herein by reference). Moreover, HGF was responsible for reducing susceptibility to irreversible EGFR TKIs in NSCLC with EGFR T790M mutations (Yamada et al., Clin Cancer Res. 2010; 16(1): 174-183, incorporated herein by reference). Recent investigations by Park et al revealed that CRIPTO1 expression in NSCLC with mutated EGFR is likely a major mechanism that leads to intrinsic resistance to EGFR TKIs. All EGFR-mutated NSCLC tumors that were resistant to erlotinib expressed higher levels of CRIPTO1, whereas only 30% of EGFR-mutated NSCLC tumors that were sensitive to erlotinib showed CRIPTO1 expression. Further in vitro studies showed that CRIPTO1-induced erlotinib resistance was linked to activation of the SRC signaling pathway via downregulation of miR-205 expression (see Park et al., J Clin Invest. 2014; 124(7):3003-3015 29, incorporated herein by reference). As a proapoptotic molecule of the Bcl-2 family, BIM is responsible for apoptosis triggered by a variety of molecules, including EGFR TKIs (Gong et al., PLoS Med. 2007; 4(10):e294, incorporated herein by reference). The BIM deletion may represent a negative predictive biomarker for tumor response in NSCLC patients treated with EGFR TKI (see Ma et al., J Cancer Res Ther. 2015; 11(2):397-402, incorporated herein by reference). A review of non-EGFR mutations that may confer resistance to EGFR-TKIs is provided for in Wang et al., Oncotargets and Therapy 2016:9; 3711-3726, incorporated herein by reference.

Determining the mutational status of EGFR-mutant cancer is well known in the art, and the FDA has approved a number of diagnostic procedures. For example, direct DNA sequencing to identify mutations in the gene encoding EGFR and non-EGFR genes are well known. Other useful mutational analysis techniques include, but are not limited to, analysis by dHPLC, DNA endonuclease (SURVEYOR) and HPLC, HRMA, massively parallel sequencing, TaqMan PCR, cycleave PCR, fragment analysis, mutation-specific PCR, mutant enriched PCR, ARMS, mutant enriched ARMS TaqMan PCR, PCR-invader, PCR-RFLP, length analysis for exon 19 deletions, in-situ LAMP with ARMS, pyrosequencing, PCR-PNA-clamp, PCR/CCP-based FRET, SmartAmp, PNA-clamp SmartAmp2, and IHC (see Ellison et al., "EGFR mutation testing in lung cancer: a review of available methods and their use for analysis of tumor tissue and cytology samples," J. Clin. Pathol. 2013; 66:79-89, incorporated herein in its entirety).

Plasma cell-free tumor DNA, or circulating tumor DNA (ctDNA), from liquid biopsy is a potential source of tumor genetic material, in the absence of tissue biopsy, for EGFR-mutational testing. Allele specific PCR, Scorpion Amplified Refractory Mutation System (ARMS) PCR, droplet digital PCR (ddPCR), and next generation sequencing (NGS) are the most commonly used technologies for mutation detection in ctDNA, and are generally known in the art. See Veldore et al., Lung Cancer (Auckl). 2018; 9: 1-11; Bordi et al., Transl Lung Cancer Res. 2015; 4(5):584-597; Fenizia et al., Future Oncol. 2015; 11(11):1611-1623; Mao et al., Medicine. 2015; 94(21):e775. doi: 10.1097/MD.0000000000000775; Marchetti et al., J Thorac Oncol. 2015; 10(10):1437-1443; Sholl et al. Arch Pathol Lab Med. doi:10.5858/arpa.2016-0163-SA; Sorber et al., Lung Cancer. 2016 May 4. pii: S0169-5002(16)30312-9. doi: 10.1016/j.lungcan.2016.04.026; Westwood et al., Health Technol Assess. 2014; 18(32):1-166; Lindeman et al., J Thorac Oncol. 2013; 8(7):823-859; Socinski et al., Clin Lung Cancer. 2010; 11(3):149-159, all incorporated herein by reference.

Selective CDK 4/6 Inhibitors

The present invention is directed to the use of a CDK4/6-specific inhibitor in combination or alternation with a EGFR-TKI inhibitor for treating a patient having an EGFR-mutant NSCLC. In particular, as contemplated herein, the CDK4/6 inhibitor is selected from Compound I, Compound II, Compound III, Compound IV, or a pharmaceutically acceptable composition, salt, isotopic analog, or prodrug thereof.

Compounds I, II, III, and IV can be prepared as previously described in WO 2014/144326, incorporated herein in its entirety.

Isotopic Substitution

The present invention includes compounds of Compound I, Compound II, Compound III, and Compound IV, with at least one desired isotopic substitution of an atom, at an amount above the natural abundance of the isotope, i.e., enriched. Isotopes are atoms having the same atomic number but different mass numbers, i.e., the same number of protons but a different number of neutrons.

By way of general example and without limitation, isotopes of hydrogen, for example, deuterium ($^2H$) and tritium ($^3H$) may be used anywhere in described structures. Alternatively, or in addition, isotopes of carbon, e.g., $^{13}C$ and $^{14}C$, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium ($^1H$), is substituted by a H-isotope, i.e., deuterium ($^2H$). Deuterium substitution can be partial or complete. Partial deuterium substitution means that at least one hydrogen is substituted by at least one deuterium. In certain embodiments, the isotope is 90, 95, or 99% or more enriched in an isotope at any location of interest. In some embodiments, it is deuterium that is 90, 95, or 99% enriched at a desired location.

Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$, $^{31}P$, $^{32}P$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

In one non-limiting embodiment, the substitution of a hydrogen atom for a deuterium atom can be provided in any of Compound I, Compound II, Compound III, or Compound IV. In one non-limiting embodiment, the substitution of a hydrogen atom for a deuterium atom occurs within a group selected from R, $R^{20}$, $R^{21}$, or $R^{22}$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$, etc.). In certain other embodiments, when two substituents are combined to form a cycle the unsubstituted carbons may be deuterated.

Epidermal Growth Factor Receptor-Tyrosine Kinase Inhibitors (EGFR-TKI)

As contemplated herein, the present invention provides methods of treating a patient with an EGFR-mutant cancer by administering a selective CDK4/6 inhibitor in combination or alternation with a EGFR-TKI as described herein. EGFR-TKIs for use in the invention include, but are not limited to, erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, lapatinib (Tykerb; GlaxoSmithKline), brigatinib (Alunbrig; Ariad Pharmaceuticals), Compound V described herein, Compound VI described herein, Compound VII described herein, sapitinib, CUDC-101, PD153035, pelitinib, AEE788 (NVP-AEE788), AST-1306, AZ5104, lifirafenib (BGB-283), canertinib, CL-387785 (EKI-785), norcantharadin, vandetanib (Caprelsa), and dacomitinib (PF-00299804; Pfizer), which are described further below.

Erlotinib (Tarveva) is a first-generation EGFR inhibitor and binds in a reversible fashion to the adenosine triphosphate (ATP) binding site of the EGFR receptor and has the chemical structure:

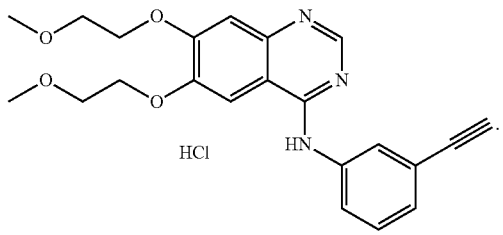 [SMILES: C#Cc1cccc(Nc2ncnc3cc(OCCOC)c(OCCOC)cc23)c1 ; Cl]

Gefitinib (Iressa) is a first-generation EGFR-TKI and binds to the adenosine triphosphate (ATP)-binding site of EGFR. Gefitinib has the chemical structure:

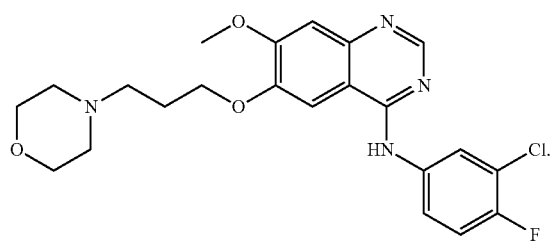 [SMILES: COc1cc2ncnc(Nc3ccc(F)c(Cl)c3)c2cc1OCCCN1CCOCC1]

Afatinib (Gilotrif) is a second-generation EGFR-TKI which irreversibly binds to and inhibits human epidermal growth factor receptors 1 and 2 (EGFR-1; HER2) and has the chemical structure:

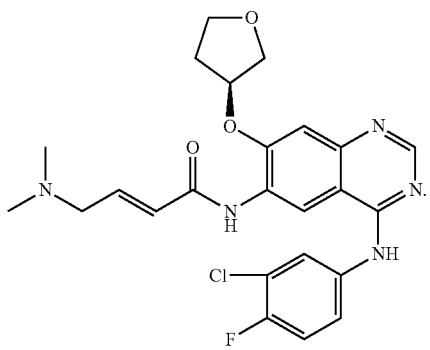 [SMILES: CN(C)C/C=C/C(=O)Nc1cc2c(Nc3ccc(F)c(Cl)c3)ncnc2cc1O[C@H]1CCOC1]

Neratinib (HKI-272 or PB272) is a second-generation, orally available, 6,7-disubstituted-4-anilinoquinoline-3-carbonitrile inhibitor of EGFR having the chemical structure:

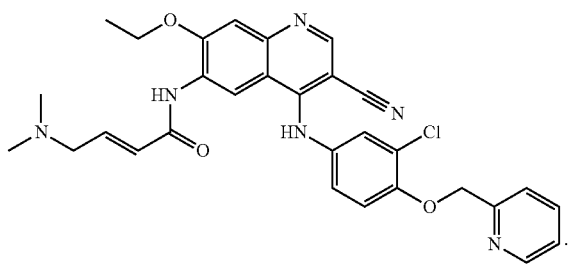 [SMILES: CCOc1cc2ncc(C#N)c(Nc3ccc(OCc4ccccn4)c(Cl)c3)c2cc1NC(=O)/C=C/CN(C)C]

Dacomitinib (PF-299 and PF-00299804) is an orally bioavailable, highly selective, second-generation small-molecule inhibitor of the pan-epidermal growth factor receptor (EGFR) family of tyrosine kinases (ErbB family) with potential antineoplastic activity. Dacomitinib specifically and irreversibly binds to and inhibits human EGFR subtypes, resulting in inhibition of proliferation and induction of apoptosis in EGFR-expressing tumor cells. Dacomitinib has the chemical structure:

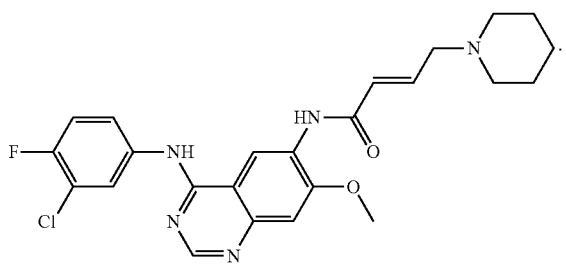 [SMILES: COc1cc2ncnc(Nc3ccc(F)c(Cl)c3)c2cc1NC(=O)/C=C/CN1CCCCC1]

Icotinib (BPI-2009; Conmana) is a third-generation EGFR-TKI quinazoline-based inhibitor of EGFR. Icotinib selectively inhibits the wild-type and several mutated forms of EGFR tyrosine kinase, and has the chemical structure:

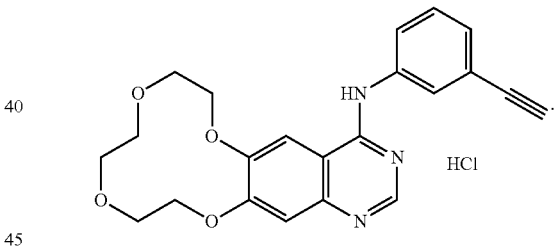

Osimertinib (AZD9291; Tagrisso) is a third-generation epidermal growth factor receptor (EGFR) tyrosine kinase inhibitor (TKI) for T790M mutated EGFR NSCLC and has the chemical structure:

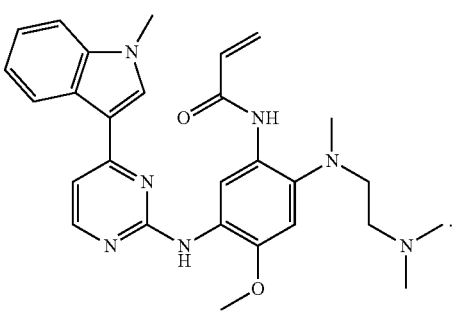 [SMILES: C=CC(=O)Nc1cc(Nc2nccc(-c3cn(C)c4ccccc34)n2)c(OC)cc1N(C)CCN(C)C]

Olmutinib (Olita) is a third-generation EGFR-TKI that acts by irreversibly blocking the epidermal growth factor receptor (EGFR), and has the chemical structure:

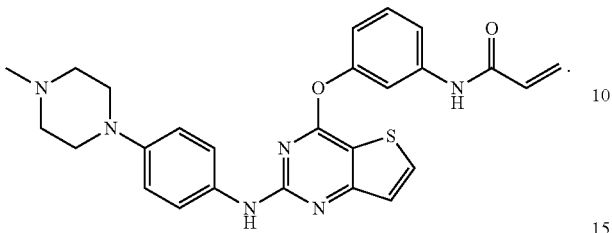

Naquotinib (ASP8273), is third-generation, mutant-selective EGFR inhibitor which covalently binds to and inhibits the activity of mutant forms of EGFR, including the T790M EGFR mutant, thereby preventing EGFR-mediated signaling, and has the chemical structure:

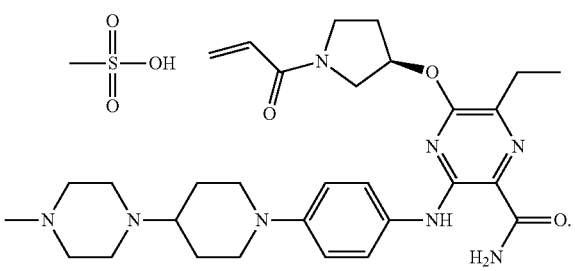

Nazartinib (EGF816) is a third-generation, irreversible, mutant-selective EGFR inhibitor which covalently binds to and inhibits the activity of mutant forms of EGFR, including the T790M EGFR mutant, thereby preventing EGFR-mediated signaling. Nazartinib has the chemical structure:

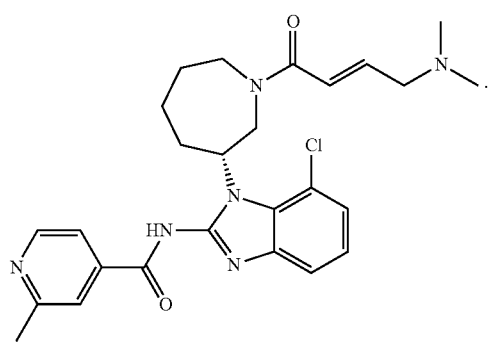 [SMILES: Cc1cc(C(=O)Nc2nc3cccc(Cl)c3n2[C@@H]2CCCCN(C(=O)/C=C/CN(C)C)C2)ccn1]

PF-06747775 is a third-generation inhibitor of the EGFR mutant form T790M. PF-06747775 specifically binds to and inhibits EGFR T790M, a secondarily acquired resistance mutation, which prevents EGFR-mediated signaling and leads to cell death in EGFR T790M-expressing tumor cells. PF-06747775 has the chemical structure:

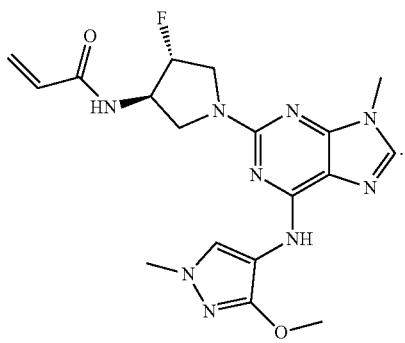 [SMILES: C=CC(=O)N[C@@H]1CN(c2nc(Nc3cn(C)nc3OC)c3ncn(C)c3n2)C[C@H]1F]

Avitinib is a third-generation EGFR-TKI which covalently binds to and inhibits the activity of mutant forms of EGFR, including the drug-resistant T790M EGFR mutant having the chemical structure:

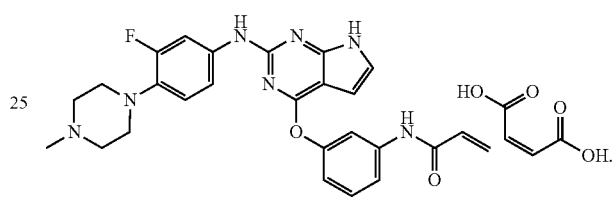

Tarloxotinib is a third-generation, irreversible EGFR-tyrosine kinase inhibitor having the chemical structure:

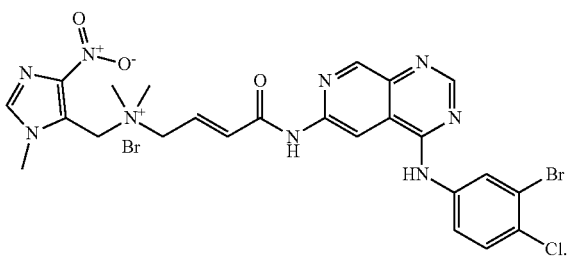 [SMILES: Cn1cnc([N+](=O)[O-])c1C[N+](C)(C)C/C=C/C(=O)Nc1cc2c(Nc3ccc(Cl)c(Br)c3)ncnc2cn1 ; Br]

PF-06459988 is an orally available third-generation, irreversible inhibitor of EGFR which specifically binds to and inhibits mutant forms of EGFR, including the secondary acquired resistance mutation T790M, which prevents EGFR-mediated signaling and leads to cell death in EGFR-mutant-expressing tumor cells. PF-06459988 has the chemical structure:

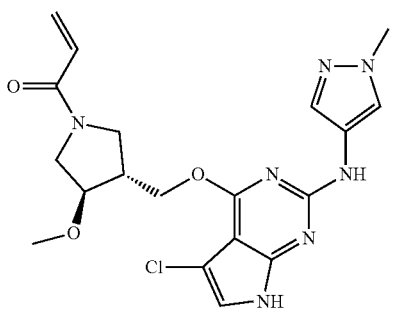

Tesevatinib (XL647, EXEL-7647 and KD-019) is an orally bioavailable EGFR inhibitor having the chemical structure:

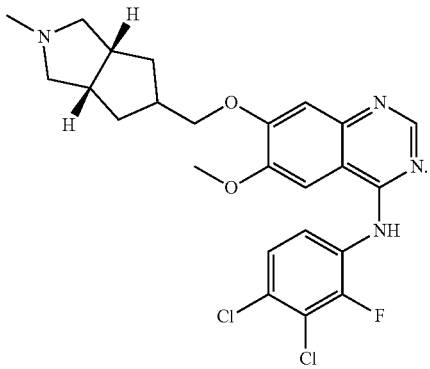 [SMILES: COc1cc2c(Nc3ccc(Cl)c(Cl)c3F)ncnc2cc1OCC1C[C@@H]2CN(C)C[C@@H]2C1]

Transtinib is a third-generation, irreversible EGFR-TKI with activity against L858R/T790M mutant NSCLC cell lines and xenografts. Transtinib has the chemical structure:

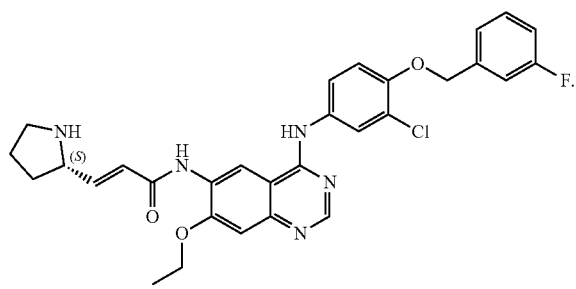

WZ-3146 is a third-generation, irreversible pyrimidine-based T790M EGFR-TKI having the chemical structure:

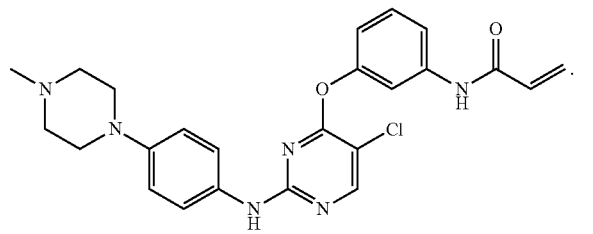 [SMILES: C=CC(=O)Nc1cccc(Oc2nc(Nc3ccc(N4CCN(C)CC4)cc3)ncc2Cl)c1]

WZ8040 is a third-generation, irreversible T790M EGFR-mutant inhibitor having the chemical structure:

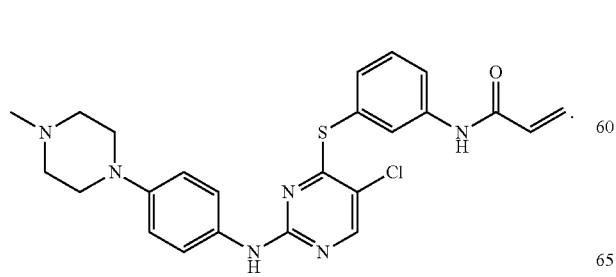

CNX-2006 is a third-generation mutant-selective EGFR inhibitor that selectively targets T790M substitution. CNX-2006 has the chemical structure:

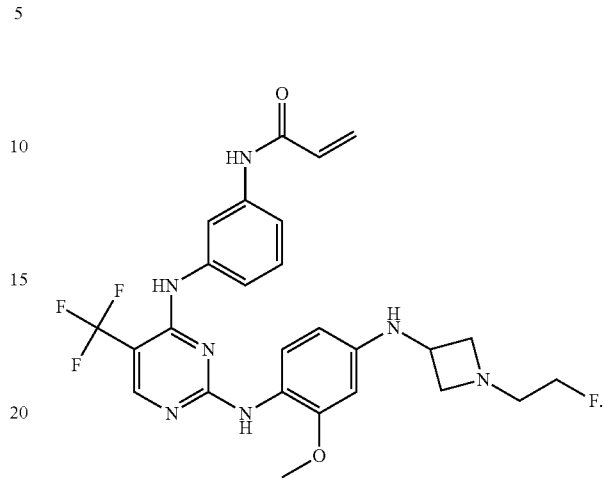

EAI045 is a fourth-generation EGFR-TKI which inhibits L858R/T790M EGFR-mutant NSCLC, as well as C797S and C797G EGFR-mutant NSCLC having the chemical structure:

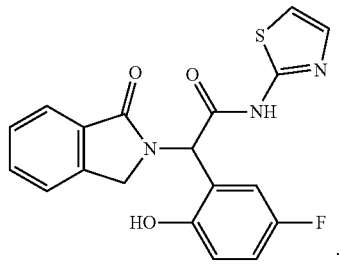 [SMILES: O=C(Nc1nccs1)C(c1cc(F)ccc1O)N1Cc2ccccc2C1=O]

Brigatinib is a dual ALK and EGFR inhibitor that has been shown to successfully inhibit the T790M/C797S/del 19 EGFR mutant, particularly in combination with an anti-EGFR antibody such as cetuximab or panitumumab (see Uchibori, K. et al. Nat. Commun. 2017, 8:14768). Brigatinib has the following structure:

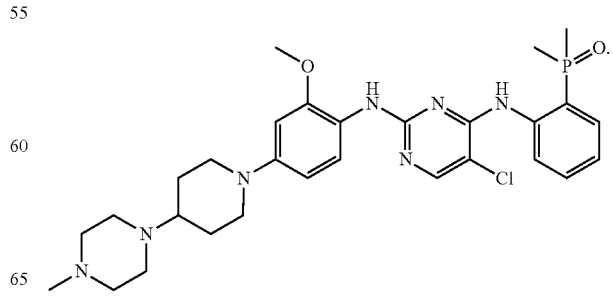

A series of 7-azaindolyl imidazole EGFR inhibitors based on the structure of a p38 inhibitor have been described that inhibit the therapy-resistant L858R/T790M/C797S mutant. Of this series, 3-(4-(4-fluorophenyl)-5-(2-phenyl-1H-pyrrolo[2,3-b]pyridin-4-yl)-1H-imidazol-2-yl)propan-1-ol (Compound VI) showed IC$_{50}$ against the mutant EGFR of 21 nM. Details of the synthesis of Compound VI can be found in Gunther, M. et al. *Angew. Chem. Int. Ed.* 2016, 55:10890-4. Compound VI has the following structure:

(Compound V)

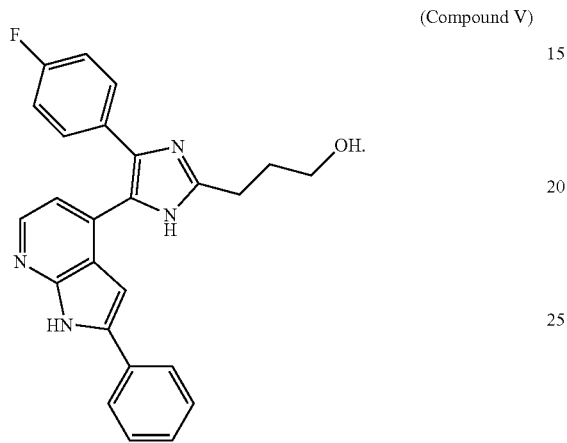

A series of pyridyl imidazole EGFR inhibitors have been described that successfully inhibit the L858R/T790M/C797S EGFR mutant. In particular, N-(3-((4-(4-(4-fluorophenyl)-2-(3-hydroxypropyl)-1H-imidazol-5-yl)pyridin-2-yl)amino)-4-methoxyphenyl)acrylamide (Compound VII) and N-(3-((4-(4-(4-fluorophenyl)-2-(3-hydroxypropyl)-1H-imidazol-5-yl)pyridin-2-yl)amino)-4-methoxyphenyl)propionamide (Compound VIII) showed IC$_{50}$ values against the L858R/T790M/C797S mutant of 8 and 7 nM, respectively. Detailed syntheses of Compound VII and Compound VIII are provided in Gunther, M. et al. *J. Med. Chem.* 2017, 60:5613-37. Compound VI and Compound VII have the following structures:

(Compound VI)

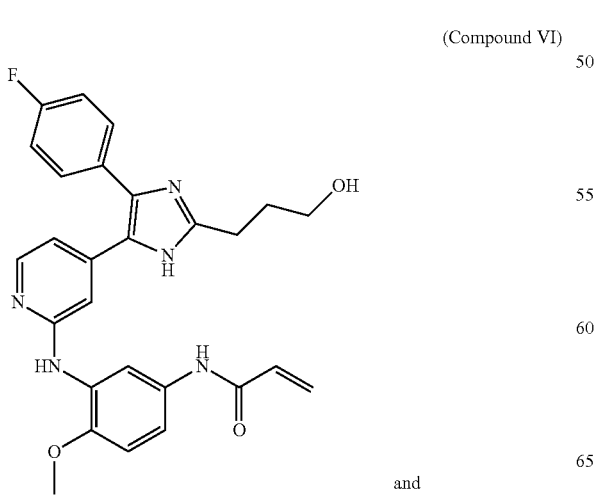

and (Compound VII)

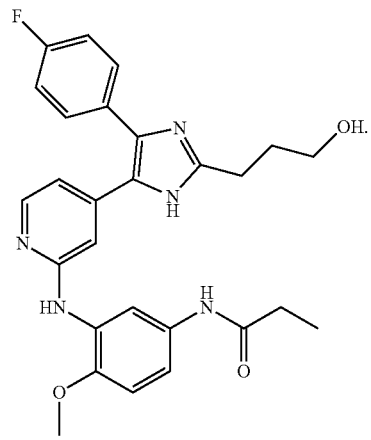

Vandetanib (Caprelsa) is an inhibitor of EGFR, VEGFR, and RET-tyrosine kinase having the chemical structure:

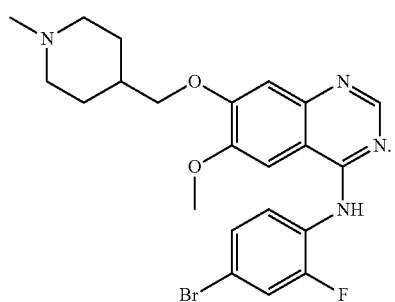 [SMILES: COc1cc2c(Nc3ccc(Br)cc3F)ncnc2cc1OCC1CCN(C)CC1]

Norcantharadin is an inhibitor of EGFR and c-Met having the chemical structure:

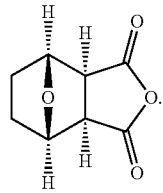

CL-387785 (EKI-785) is a selective, irreversible EGFR inhibitor having the chemical structure:

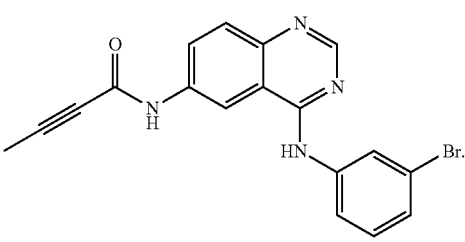 [SMILES: CC#CC(=O)Nc1ccc2ncnc(Nc3cccc(Br)c3)c2c1]

Canertinib is an irreversible inhibitor of EGFR, Her-2, and ErbB4 having the chemical structure:

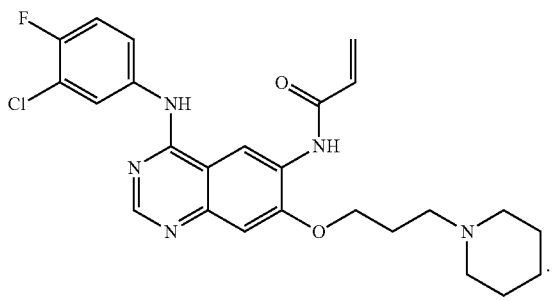 [SMILES: C=CC(=O)Nc1cc2c(Nc3ccc(F)c(Cl)c3)ncnc2cc1OCCCN1CCCCC1]

Lifirafenib (BGB-283) is a potent inhibitor of EGFR and RAF having the chemical structure:

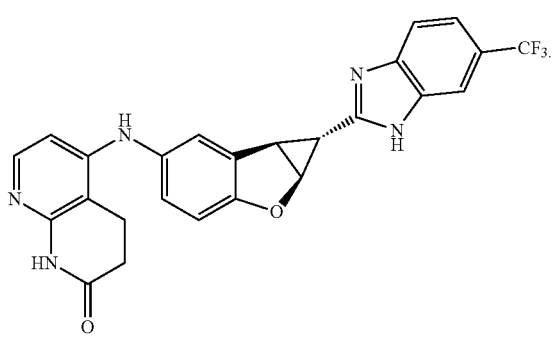 [SMILES: O=C1CCc2c(Nc3ccc4c(c3)[C@@H]3[C@H](O4)[C@H]3c3nc4ccc(C(F)(F)F)cc4[nH]3)ccnc2N1]

AZ5104 is a potent inhibitor of both wild-type and mutant (L858R/T790M, L858R, L861Q) EGFR having the chemical structure:

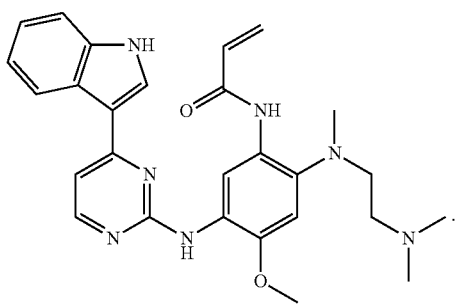 [SMILES: C=CC(=O)Nc1cc(Nc2nccc(-c3c[nH]c4ccccc34)n2)c(OC)cc1N(C)CCN(C)C]

AST-1306 is an irreversible inhibitor of EGFR (including the T790M/L858R mutation) and ErbB2 having the chemical structure:

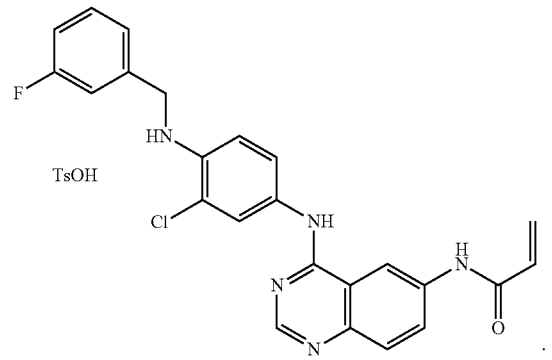

AEE788 (NVP-AEE788) is a potent inhibitor of EGFR and HER2/ErbB2 having the chemical structure:

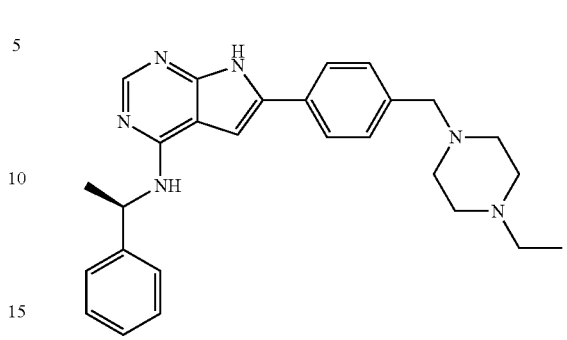

Pelitinib is a potent irreversible inhibitor of EGFR having the chemical structure:

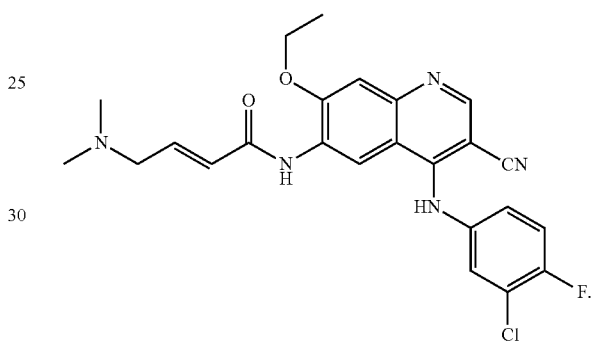

PD153035 is a potent and specific inhibitor of EGFR having the chemical structure:

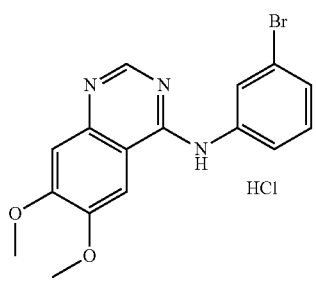

CUDC-101 is a potent inhibitor of EGFR, HDAC, and HER2 having the chemical structure:

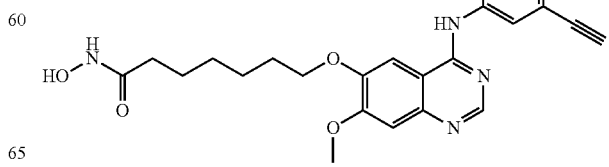

Sapitinib (AZD8931) is a reversible inhibitor of EGFR, ErbB2, and ErbB3 having the chemical structure:

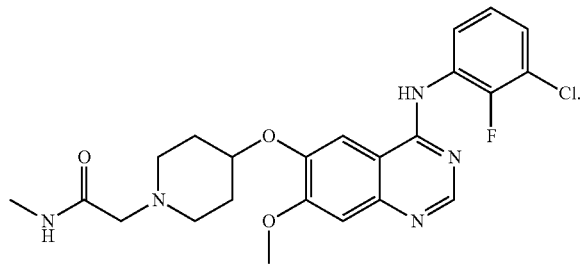 [SMILES: CNC(=O)CN1CCC(Oc2cc3c(Nc4cccc(Cl)c4F)ncnc3cc2OC)CC1]

Lapatinib (Tykerb) reversibly blocks phosphorylation of the epidermal growth factor receptor (EGFR), ErbB2, and the Erk-1 and-2 and AKT kinases; it also inhibits cyclin D protein levels in human tumor cell lines and xenografts. EGFR and ErbB2 have been implicated in the growth of various tumor types having the structure:

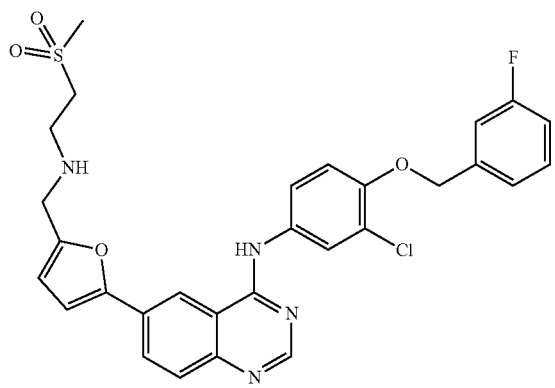 [SMILES: CS(=O)(=O)CCNCc1ccc(-c2ccc3ncnc(Nc4ccc(OCc5cccc(F)c5)c(Cl)c4)c3c2)o1]

Pharmaceutical Compositions and Dosage Forms

In other aspects, this invention is a pharmaceutical composition comprising a therapeutically effective amount of a selective CDK4/6 inhibitor selected from Compound I, Compound II, Compound III, and Compound IV and an EGFR-TKI, and one or more pharmaceutically acceptable diluents, preservatives, solubilizers, emulsifiers, adjuvants, excipients, or carriers. Such excipients include liquids such as water, saline, glycerol, polyethylene glycol, hyaluronic acid, ethanol, and the like.

The term "pharmaceutically acceptable carrier" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation. "Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

In general, the compositions of the disclosure will be administered in a therapeutically effective amount by any of the accepted modes of administration. Suitable dosage ranges depend upon numerous factors such as the severity of the disease to be treated, the age and relative health of the patient, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in an acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacterium retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition will be delivered to the patient. The precise effective amount will vary from patient to patient and will depend upon the species, age, the patient's size and health, the nature and extent of the condition being treated, recommendations of the treating physician, and the therapeutics or combination of therapeutics selected for administration. the effective amount for a given situation can be determined by routine experimentation. For purposes of the disclosure, a therapeutic amount may for example be in the range of about 0.01 mg/kg to about 250 mg/kg body weight, more preferably about 0.1 mg/kg to about 10 mg/kg, in at least one dose. In larger mammals, the indicated daily dosage can be from about 1 mg to 1500 mg, one or more times per day, more preferably in the range of about 10 mg to 600 mg. The patient can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms with at least 5, 10, 15, 20, 25, 50, 100, 200, 250, 300, 400, 500, 600, 700, or 750 mg of active compound, or its salt. The pharmaceutical composition may also include a molar ratio of the active compound and an additional active agent, in a ratio that achieves the desired results.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Methods of Treatment

A method of treating a patient, for example a human, with an EGFR-mutant cancer are provided herein.

In one aspect of the invention, provided herein is a method of treating a patient with an EGFR-mutant cancer by administering a therapeutically effective amount of a selective CDK 4/6 inhibitor described herein in combination with an effective amount of an EGFR-TKI, wherein the patient is EGFR-TKI treatment naïve, that is, the patient has not been exposed to an EGFR-TKI. The EGFR-mutant cancer can be any cancer wherein the development of the cancer is at least partly attributable to a driving EGFR-mutation. Cancers that may be driven by EGFR-mutations include bladder cancer, gliomas including glioblastoma, head and neck cancer, breast cancer, cervical cancer, uterine cancer, colon and colorectal cancer, gastroesophageal cancer, non-small cell lung carcinoma (NSCLC), prostate cancer, ovarian cancer, pancreatic cancer, renal cell carcinoma, squamous cell carcinoma, and thyroid cancer. In one embodiment, the cancer is NSCLC. In one embodiment, the cancer is breast cancer. In one embodiment, the cancer is gastroesophogeal cancer. In one embodiment, the cancer is head and neck cancer. In one embodiment, the EGFR-TKI is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, lapatinib (Tykerb; GlaxoSmithKline), brigatinib (Alunbrig; Ariad Pharmaceuticals), Compound V described herein, Compound VI described herein, Compound VII described herein, sapitinib, CUDC-101, PD153035, pelitinib, AEE788 (NVP-AEE788), AST-1306, AZ5104, lifirafenib (BGB-283), canertinib, CL-387785 (EKI-785), norcantharadin, vandetanib (Caprelsa), and dacomitinib (PF-00299804; Pfizer), or a combination thereof or a combination thereof. In one embodiment, the CDK 4/6 inhibitor is selected from Compounds I, II, III, or IV. In a particular embodiment, the cancer is a NSCLC, the CDK 4/6 inhibitor is Compound IV, and the EGFR-TKI is osimertinib.

In one alternative aspect of the invention, provided herein is a method of treating a patient with an EGFR-mutant cancer by administering a therapeutically effective amount of a selective CDK 4/6 inhibitor described herein in combination with an effective amount of an EGFR-TKI, wherein the patient is EGFR-TKI treatment naïve and the cancer harbors an EGFR mutation that renders it resistant to EGFR-TKI treatment. EGFR-mutations that render a cancer EGFR-TKI intrinsically resistant or primarily resistant are known in the art and described herein. In one embodiment, the patient's cancer harbors an EGFR exon 20 insertion mutation. In one embodiment, the exon 20 insertion occurs between amino acids 767 to 774. In one embodiment, the exon 20 insertion is D770_N771insNPG. In one embodiment, the EGFR mutation is a G719X or L861X mutation, wherein X represents a different amino acid, for example but not limited to alanine, cysteine, or serine. In one embodiment, the EGFR mutation is selected from V843I, L747S, D761Y, V769M, T854A, and A871E. In one embodiment, the selective CDK 4/6 inhibitor administered is Compound IV. In one embodiment, the EGFR-TKI is selected from erlotinib, gefitinib, afatinib, brigatinib, lapatinib, and osimertinib. In one embodiment, the EGFR-TKI is osimertinib.

In one alternative aspect of the invention, provided herein is a method of treating a patient with an EGFR-mutant NSCLC by administering a therapeutically effective amount of a selective CDK 4/6 inhibitor described herein in combination with an effective amount of the EGFR-TKI osimertinib, wherein the patient is EGFR-TKI treatment naïve and the NSCLC harbors a T790M EGFR mutation. In one embodiment, the selective CDK 4/6 inhibitor administered is Compound IV.

In one alternative aspect of the invention, provided herein is a method of treating a patient with an EGFR-mutant cancer by administering a therapeutically effective amount of a selective CDK 4/6 inhibitor described herein in combination with an effective amount of an EGFR-TKI, wherein the patient is EGFR-TKI treatment naïve and the NSCLC harbors a non-EGFR mutation that renders it resistant to EGFR-TKI treatment. Non-EGFR mutations that render an EGFR-mutant cancer intrinsically or primarily resistant are generally known in the art. In one embodiment, the cancer is NSCLC and the non-EGFR mutation is selected from: a BRAF mutation; a PIK3CA mutation; a MAPK1 amplification; a MET amplification; a HER2 amplification; an increased expression in KDM5, FGF2, FGFR1, AXL, ROR1, Notch-1; an increased activation in NFκB, Wnt-tnkyrase-β-catenin, JAK2, or VEGFR; up-regulation of ADAM17; down-regulation of DAPK or NF-1; loss of expression of IGF binding proteins; loss of PTEN expression or function; MLH1 V384D polymorphism; a KRAS mutation; germline deletion polymorphism of BIM; microRNA expression of miR-21, miR-271, and miR-218; increased HGF expression; CRIPTO1 expression; and SCLC transformation. In one embodiment, the selective CDK 4/6 inhibitor administered is Compound IV. In one embodiment, the EGFR-TKI is selected from erlotinib, gefitinib, afatinib, brigatinib, lapatinib, and osimertinib. In one embodiment, the EGFR-TKI is osimertinib. In one embodiment, the EGFR-TKI administered is afatinib. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect of the invention, provided herein is a method of treating a patient with an EGFR-mutant cancer by administering a therapeutically effective amount of a selective CDK 4/6 inhibitor described herein in combination with an effective amount of an EGFR-TKI, wherein the patient is EGFR-TKI treatment naïve and the cancer harbors an EGFR-mutation and a non-EGFR mutation that renders it resistant to EGFR-TKI treatment In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect, provided herein is a method of treating a patient with an EGFR-mutant cancer which includes:

a) administering to the patient an EGFR-TKI;

b) monitoring the patient's EGFR-mutational status; and, c) administering to the patient a selective CDK 4/6 inhibitor described herein in combination with the EGFR-TKI upon the detection of an EGFR mutation or non-EGFR mutation that confers resistance upon the cancer to the inhibitory effects of EGFR-TKI. Monitoring EGFR-mutational status during treatment can be performed using any standard or customary assay as known. For example, mutational status can be monitored using solid tumor biopsy assays or plasma-based assays such as ctDNA assays. In one embodiment, the EGFR-TKI is selected from gefitinib, erlotinib, afitinib, or osimertinib. In one embodiment, the CDK 4/6 inhibitor is Compound IV. In one embodiment, the EGFR-mutant cancer is NSCLC. In one embodiment, the EGFR-mutant cancer is breast cancer. In one embodiment, the EGFR-mutant cancer is head and neck cancer. In one embodiment, the EGFR-mutant cancer is esophageal cancer.

In one alternative aspect, provided herein is a method of treating a patient with an EGFR-mutant NSCLC which includes:
a) administering to the patient EGFR-TKI osimertinib;
b) monitoring the patient's NSCLC EGFR-mutational status; and,
c) administering to the patient a selective CDK 4/6 inhibitor described herein in combination with osimertinib upon the detection of an EGFR mutation or non-EGFR mutation that confers resistance upon the NSCLC to the inhibitory effects of osimertinib. In one embodiment, the selective CDK 4/6 inhibitor administered is Compound IV. In one embodiment, the mutation is an EGFR C797 mutation, for example C797S or C797G, an EGFR G796D mutation, an EGFR L718V mutation, or the loss of an EGFR T790M mutation. In one embodiment, the non-EGFR mutation is MET amplification or SCLC transformation. In one embodiment, the non-EGFR-mutation is a BRAF, a PIK3CA mutation, a KRAS mutation, a CCDC6-RET fusion, or a FGFR3-TACC fusion. In one embodiment, the BRAF mutation is V600E. In one embodiment, the KRAS mutation is Q61K. In one embodiment, the PIK3CA mutation is E545K, R88Q, or N345K.

In one alternative aspect, provided herein is a method of treating a patient with an EGFR-mutant NSCLC which includes:
a) administering to the patient the EGFR-TKI osimertinib;
b) monitoring the patient's NSCLC response to osimertinib;
c) administering to the patient a selective CDK 4/6 inhibitor described herein in combination with osimertinib upon the detection of the patient's NSCLC becoming non-responsive to osimertinib. In one embodiment, the selective CDK 4/6 inhibitor administered is Compound IV. In one embodiment, the non-responsiveness is NSCLC disease progression.

In certain aspects, the patient has an EGFR-mutant cancer, for example, but not limited to, a T790M, T790M/C797S, or T790M/C797G EGFR-mutant cancer is provided including administering, in combination or alternation, an EGFR-TKI and selective CDK4/6 inhibitor selected from Compound I, Compound II, Compound III, and Compound IV. The use of a selective CDK4/6 inhibitor in combination or alternation with a EGFR-TKI has been shown to reduce or delay the development of EGFR-TKI acquired resistance in EGFR-mutant NSCLS. In addition, the use of a CDK4/6 inhibitor in combination or alternation with an EGFR-TKI has been shown to reestablish the sensitivity of an EGFR-mutant NSCLC that has developed an acquired resistance to an EGFR-TKI to the inhibitory effects of the EGFR-TKI. In a further embodiment, the use of a selective CDK4/6 inhibitor in combination or alternation with an EGFR-TKI extends the period of efficacious use of an EGFR-TKI. In one embodiment, the cancer is NSCLC.

In one embodiment, the CDK4/6 inhibitor and EGFR-TKI are administered to a patient having a NSCLC harboring an EGFR-mutation exon 21 L858R substitution. In one embodiment, the CDK4/6 inhibitor and EGFR-TKI are administered to a patient having a NSCLC harboring an EGFR-mutation exon 21 L858R substitution, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation exon 19 LREA deletion. In one embodiment, the CDK4/6 inhibitor and EGFR-TKI are administered to a patient having a NSCLC harboring an EGFR-mutation exon 19 LREA deletion, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation exon 19 VAIKEL insertion. In one embodiment, the CDK4/6 inhibitor and EGFR-TKI are administered to a patient having a NSCLC harboring an EGFR-mutation exon 19 VAIKEL insertion, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation G719X substitution, wherein X is an amino acid selected from alanine, cysteine, or serine. In one embodiment, the CDK4/6 inhibitor and EGFR-TKI are administered to a patient having a NSCLC harboring an EGFR-mutation G719X substitution, wherein X is an amino acid selected from alanine, cysteine, or serine, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation L861X substitution, wherein X is an amino acid selected from alanine, cysteine, or serine. In one embodiment, the CDK4/6 inhibitor and EGFR-TKI are administered to a patient having a NSCLC harboring an EGFR-mutation L861X substitution, wherein X is an amino acid selected from alanine, cysteine, or serine, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation V765A substitution. In one embodiment, the CDK4/6 inhibitor and EGFR-TKI are administered to a patient having a NSCLC harboring an EGFR-mutation V765A substitution, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation T783A substitution. In one embodiment, the CDK4/6 inhibitor and EGFR-TKI are administered to a patient having a NSCLC harboring an EGFR-mutation T783A substitution, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation S784P substitution. In one embodiment, the CDK4/6 inhibitor and EGFR-TKI are administered to a patient having a NSCLC harboring an EGFR-mutation S784P substitution, wherein, at the time of the first administration, the patient is EGFR-TKI naïve. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation T790M substitution. In one embodiment, the CDK4/6 inhibitor and EGFR-TKI are administered to a patient having a NSCLC harboring an EGFR-mutation T790M substitution, wherein, at the time of the first administration, the patient is EGFR-TKI naïve. In one embodiment, the CDK4/6 inhibitor and EGFR-TKI are administered to a patient having a NSCLC harboring an EGFR-mutation T790M substitution, wherein, at the time of the first administration, the patient has developed an acquired resistance to one or more EGFR-TKIs. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation T854A substitution. In one embodiment, the CDK4/6 inhibitor and EGFR-TKI are administered to a patient having a NSCLC harboring an EGFR-mutation T854A substitution, wherein, at the time of the first administration, the patient has developed an acquired resistance to one or more EGFR-TKIs. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation D761Y substitution. In one embodiment, the CDK4/6 inhibitor and EGFR-TKI are administered to a patient having a NSCLC harboring an EGFR-mutation D761Y substitution, wherein, at the time of the first administration, the patient has developed an acquired resistance to one or more EGFR-TKIs. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation L747S substitution. In one embodiment, the CDK4/6 inhibitor and EGFR-TKI are administered to a patient having a NSCLC harboring an EGFR-mutation L474S substitution, wherein, at the time of the first administration, the patient has developed an acquired resistance to one or more EGFR-TKIs. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation C797S substitution. In one embodiment, the CDK4/6 inhibitor and EGFR-TKI are administered to a patient having a NSCLC harboring an EGFR-mutation C797S substitution, wherein, at the time of the first administration, the patient has developed an acquired resistance to one or more EGFR-TKIs. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation C797G substitution. In one embodiment, the CDK4/6 inhibitor and EGFR-TKI are administered to a patient having a NSCLC harboring an EGFR-mutation C797G substitution, wherein, at the time of the first administration, the patient has developed an acquired resistance to one or more EGFR-TKIs. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a NSCLC harboring an EGFR-mutation, wherein the NSCLC has acquired resistance to one or more EGFR-TKIs. In one embodiment, the CDK4/6 inhibitor and EGFR-TKI are administered to a patient having a NSCLC harboring an EGFR-mutation, wherein the NSCLC has acquired resistance to an EGFR-TKI selected from erlotinib, gefitinib, afatinib, neratinib, and dacomitinib. In one embodiment, the CDK4/6 inhibitor and EGFR-TKI are administered to a patient having a NSCLC harboring an EGFR-mutation, wherein the NSCLC has acquired resistance to an EGFR-TKI selected from osimertinib, olmutinib, naquotinib, nazartinib, PF-06747775, icotinib, neratinib, avitinib, EAI045, tarloxotinib, PF-06459988, tesevatinib, transtinib, WZ-3146, WZ8040, brigatinib, and CNX-2006. In one embodiment, the CDK4/6 inhibitor and EGFR-TKI are administered to a patient having a NSCLC harboring an EGFR-mutation, wherein the NSCLC has acquired resistance to an EGFR-TKI selected from osimertinib, olmutinib, naquotinib, nazartinib, PF-06747775, icotinib, neratinib, avitinib, EAI045, tarloxotinib, PF-06459988, tesevatinib, transtinib, WZ-3146, WZ8040, brigatinib, and CNX-2006, and is administered an EGFR-TKI selected from erlotinib, gefitinib, afatinib, neratinib, and dacomitinib.

In one embodiment, the CDK4/6 inhibitor and EGFR-TKI are administered to a patient, for example a human, having an EGFR-mutant NSCLC that has acquired resistance to an EGFR-TKI as a result of a non-EGFR mutation. In one embodiment, the CDK4/6 inhibitor and EGFR-TKI are administered to a patient having an EGFR-mutant NSCLC that has acquired resistance to an EGFR-TKI as a result of a Her2 amplification or mutation, Met amplification, HGF overexpression, IGF-1R activation, PTEN loss of function mutations, BIM mutations, CRIPTO 1 expression, and/or P13k activation, wherein, at the time of the first administration, the patient has developed an acquired resistance to one or more EGFR-TKIs. In one embodiment, the EGFR-TKI administered is erlotinib. In one embodiment, the EGFR-TKI administered is gefitinib. In one embodiment, the EGFR-TKI administered is afatinib. In one embodiment, the EGFR-TKI administered is neratinib. In one embodiment, the EGFR-TKI administered is dacomitinib. In one embodiment, the EGFR-TKI administered is rociletinib. In one embodiment, the EGFR-TKI administered is osimertinib. In one embodiment, the EGFR-TKI administered is olmutinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI is EAI045. In one embodiment, the EGFR-TKI is tarloxotinib. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK4/6 inhibitor administered is Compound IV. In any one of the preceding embodiments, the patient is a human.

In one embodiment, the CDK4/6 inhibitor and EGFR-TKI are administered to a patient, for example a human, having a T790M EGFR-mutant NSCLC that has acquired resistance to an EGFR-TKI as a result of a non-EGFR mutation. In one embodiment, the CDK4/6 inhibitor and EGFR-TKI are administered to a patient having a T790M EGFR-mutant NSCLC that has acquired resistance to an EGFR-TKI as a result of a Her2 amplification or mutation, Met amplification, HGF overexpression, IGF-1R activation, PTEN loss of function mutations, BIM mutations, CRIPTO 1 expression, and/or P13k activation, wherein, at the time of the first administration, the patient has developed an acquired resistance to one or more EGFR-TKIs. In one embodiment, the EGFR-TKI administered is rociletinib. In one embodiment, the EGFR-TKI administered is osimertinib. In one embodiment, the EGFR-TKI administered is naquotinib. In one embodiment, the EGFR-TKI administered is nazatinib. In one embodiment, the EGFR-TKI administered is PF-06747775. In one embodiment, the EGFR-TKI administered is icotinib. In one embodiment, the EGFR-TKI administered is neratinib. In one embodiment, the EGFR-TKI administered is avitinib. In one embodiment, the EGFR-TKI administered is EAI045. In one embodiment, the EGFR-TKI administered is PF-06459988. In one embodiment, the EGFR-TKI administered is tesevatinib. In one embodiment, the EGFR-TKI administered is transtinib. In one embodiment, the EGFR-TKI administered is WZ-3146. In one embodiment, the EGFR-TKI administered is WZ8040. In one embodiment, the EGFR-TKI administered is CNX-2006. In one embodiment, the EGFR-TKI administered is brigatinib. In one embodiment, the CDK 4/6 inhibitor is Compound IV. In any one of the preceding embodiments, the patient is a human.

Synthesis of Select CDK4/6 Inhibitors

CDK4/6 Inhibitors of the present invention can be synthesized by any means known to those of ordinary skill in the art, including for example, according to the generalized Scheme below.

General Synthetic Scheme 1:

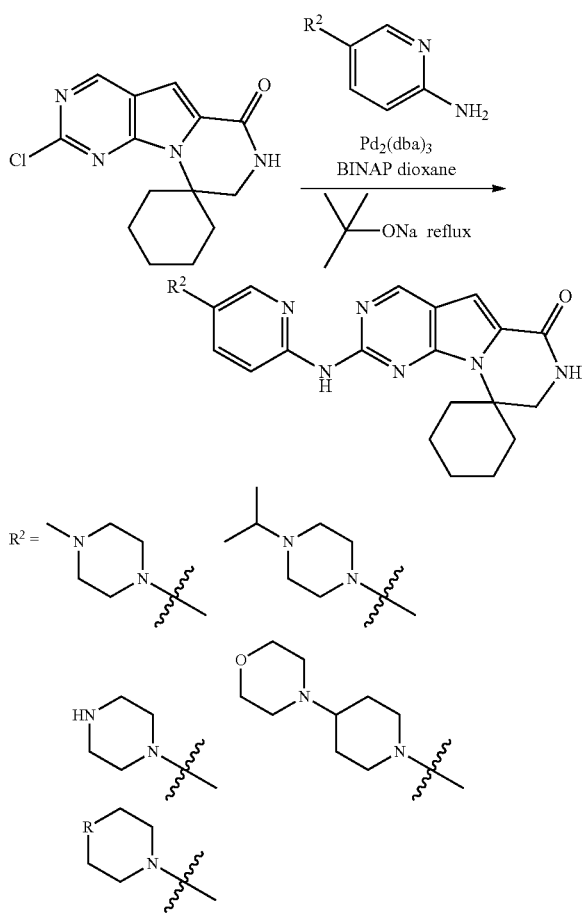

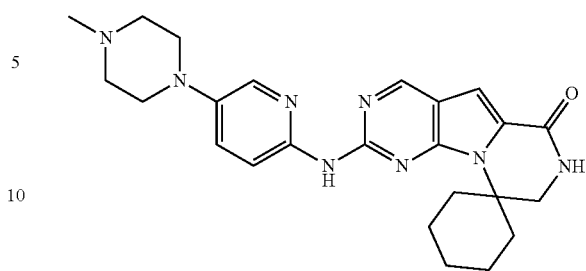

Compound II

Compound II was synthesized using synthetic Scheme 1 as described in U.S. Pat. No. 8,598,197. 1H NMR (600 MHz, DMSO-$d_6$) ppm 1.27-1.44 (br. m., 9H) 1.79-1.87 (br. m., 5H) 2.62-2.69 (br. m., 2H) 3.16-3.36 (br. m., 4H) 3.63-3.73 (m., 5H) 3.85-3.89 (br. m., 2H) 7.11 (s, 1H) 7.31 and 7.28 (d., 1H) 7.69 and 7.70 (d., 1H) 7.86, 7.86, 7.88, 7.89 (dd., 1H) 8.81 (s., 1H) LCMS (ESI) 447 (M+H).

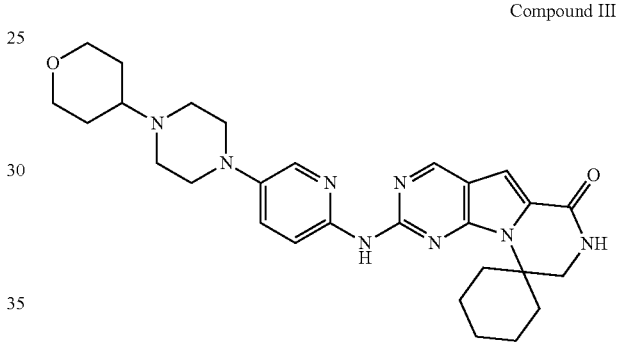

Compound III

Compound III was synthesized using synthetic Scheme 1 as described in U.S. Pat. No. 8,598,197. $^1$H NMR (600 MHz, DMSO-$d_6$) δ ppm 0.84 (t, J=7.61 Hz, 2H) 1.13-1.39 (m, 4H) 1.46 (d, J=14.05 Hz, 2H) 1.64-1.99 (m, 6H) 2.21 (br. s., 1H) 2.66-2.89 (m, 2H) 3.06 (br. s., 1H) 3.24-3.36 (m, 1H) 3.37-3.50 (m, 2H) 3.56-3.72 (m, 2H) 3.77-4.00 (m, 4H) 4.02-4.19 (m, 2H) 7.25 (s, 1H) 7.50-7.75 (m, 2H) 7.89 (d, J=2.93 Hz, 1H) 8.14 (d, J=7.32 Hz, 1H) 8.38 (br. s., 1H) 9.06 (s, 1H) 11.53 (br. s., 1H). LCMS ESI (M+H) 517.

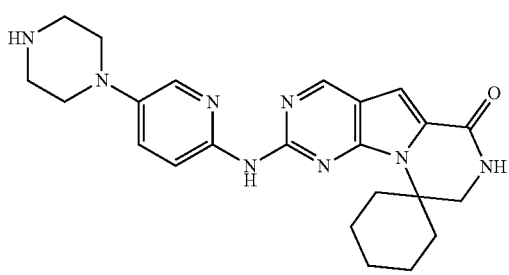

Compound I

Compound I was synthesized using synthetic Scheme 1 as described in U.S. Pat. No. 8,598,197. 1H NMR (600 MHz, DMSO-$d_6$) ppm 1.27-1.64 (m, 6H) 1.71 (br. s., 2H) 1.91 (br. s., 2H) 2.80 (br. s., 1H) 3.17-3.24 (m, 2H) 3.41 (br. s., 4H) 3.65 (br. s., 4H) 7.26 (br. s., 1H) 7.63 (br. s., 1H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS (ESI) 433 (M+H).

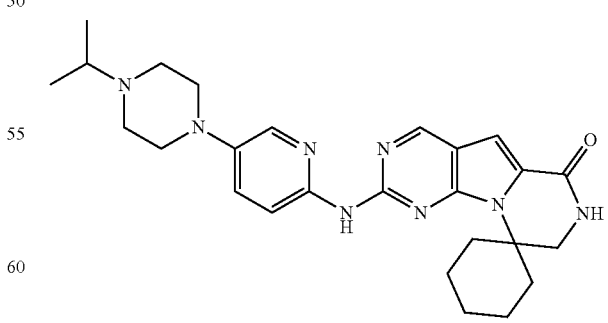

Compound IV

Compound IV was synthesized using the conditions of synthetic Scheme 1 as described in U.S. Pat. No. 8,598,197. 1H NMR (400 MHz, D20) ppm 1.47 (br. s., 6H) 1.72 (br. s., 2H) 1.92 (br. s., 2H) 2.77 (br. s., 3H) 3.18 (br. s., 2H) 3.46

(br. s., 2H) 3.63 (br. s., 2H) 3.66 (d, J=6.15 Hz, 2H) 3.80 (br. s., 2H) 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS (ESI) 447 (M+H).

Example 1

The Effect of Compound IV in Combination with Afatinib in an EGFR$^{L858R/T790M}$ NSCLC Model.

Compound IV in combination with the EGFR-TKI afatinib was tested in an EGFR$^{L858R/T790M}$ NSCLC model. The combination of Compound IV in dosages of 50 mg/kg and 100 mg/kg+afatinib was tested and compared to treatment regimens consisting of only Compound IV (in 50 mg/kg dose or a 100 mg/kg) or afatinib (20 mg/kg). H1975 (EGFR$^{L858R/T790M}$ NSCLC Model) tumor bearing mice were treated daily. Tumors were measured twice a week until vehicle treated mice tumors reached about 1000 mm$^3$ (18 days). Data is plotted to compare tumor growth in each cohort during the 18 days of treatment.

Compound IV when administered at either 50 mg/kg or 100 mg/kg in combination with afatinib increased the afatinib efficacy and extended the time to resistance in the EGFR$^{L858R/T790M}$ NSCLC model. The combination treatment was more effective at decreasing tumor volume than treatment that only consisted of both Compound IV alone and afatinib alone. Results are shown in FIG. 1.

Example 2

The Effect of Compound IV in Combination with Erlotinib in an EGFR$^{L858R/T790M}$ NSCLC Model.

Compound IV in combination with the EGFR-TKI erlotinib was tested in an EGFR$^{L858R/T790M}$ NSCLC model. The combination of Compound IV in dosages of 50 mg/kg and 100 mg/kg+erlotinib was tested and compared to treatment regimens consisting of only Compound IV (in 50 mg/kg dose or a 100 mg/kg) or erlotinib (70 mg/kg). H1975 (EGFR$^{L858R/T790M}$ NSCLC Model) tumor bearing mice were treated daily. Tumors were measured twice a week until vehicle treated mice tumors reached about 1000 mm$^3$ (18 days). Data is plotted to compare tumor growth in each cohort during the 18 days of treatment.

Figure 2:
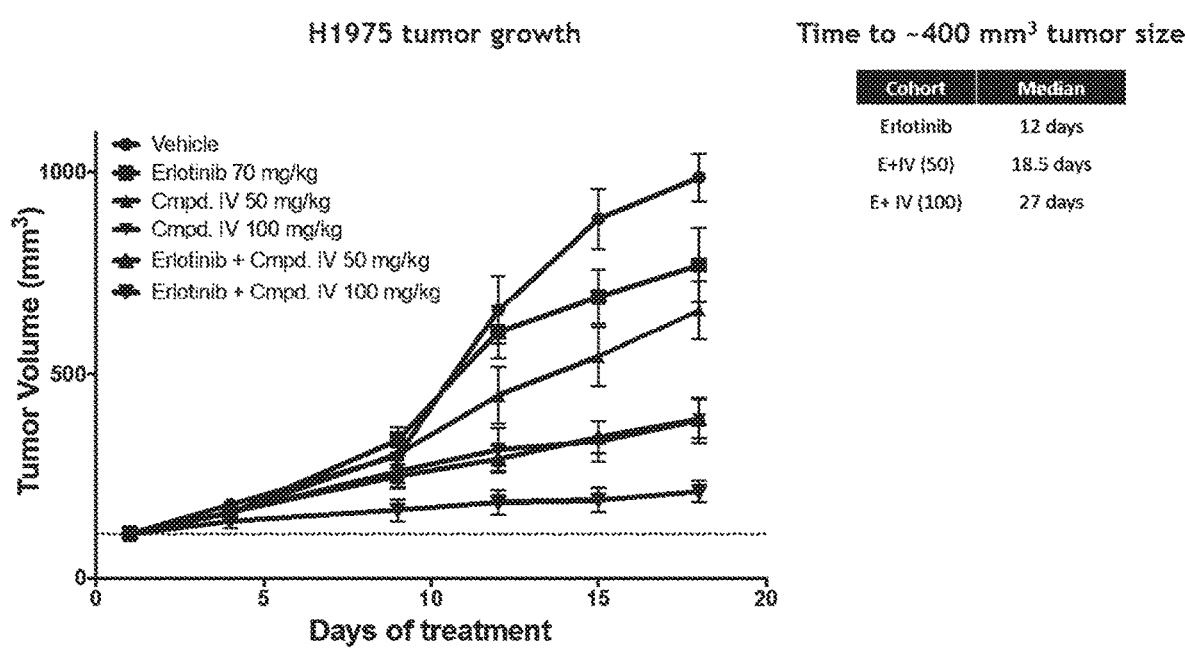
FIG. 2 is a graph showing the addition of a CDK4/6 inhibitor (Compound IV) reverses EGFR-TKI acquired resistance to the EGFR-TKI compound afatinib in an EGFR L858R/T790M NSCLC model as described in Example 2. The x-axis is days of treatment measured in time and the y-axis is tumor volume measured in $mm^3$.
Figure 3:
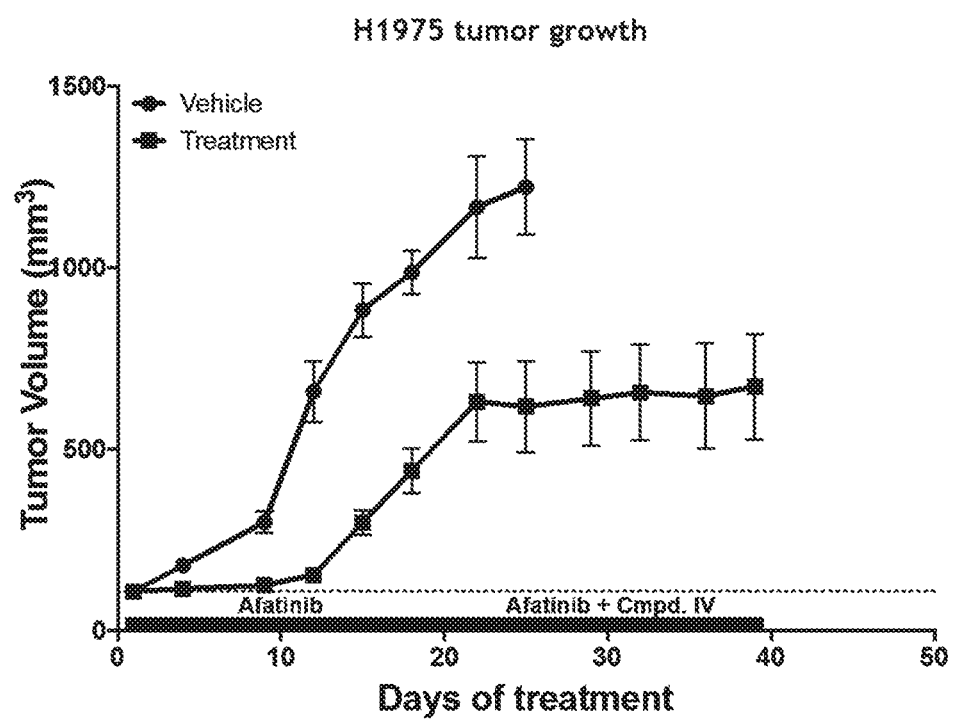
FIG. 3 is a graph showing the addition of CDK4/6 inhibitor (Compound IV) reverses acquired resistance to afatinib. EGFRL858R/T790M NSCLC model (H1975) tumor bearing mice were treated with daily oral doses of vehicle or afatinib (20 mg/kg). Once tumors became resistant to afatinib (~D18), Compound IV (100 mg/kg) was added to the treatment regimen. Tumors were measured twice for 40 days. Data is plotted to compare tumor growth in each cohort during the treatment. The x-axis is days of treatment measured in time and the y-axis is tumor volume measured in $mm^3$.

Compound IV when administered at either 50 mg/kg or 100 mg/kg in combination with erlotinib reversed erlotinib resistance in the EGFR$^{L858R/T790M}$ NSCLC model. Results are shown in FIG. 2.

Example 3

The Effect of Compound IV in Combination with Afatinib in an EGFR$^{L858R/T790M}$ NSCLC Model.

Compound IV in combination with the EGFR-TKI afatinib was tested in an EGFR$^{L858R/T790M}$ NSCLC model to determine the ability of the combination to reverse afatinib resistance. H1975 (EGFR$^{L858R/T790M}$ NSCLC Model) tumor bearing mice were treated daily with 20 mg/kg of afatinib. Once tumors became resistant to afatinib (about D18), Compound IV (100 mg/kg) was added to the treatment regimen. Tumors were measured twice a week for 40 days. Data is plotted to compare tumor growth in each cohort during treatment.

Compound IV when administered at either 50 mg/kg or 100 mg/kg in combination with afatinib increased the afatinib efficacy and extended the time to resistance in the EGFR$^{L858R/T790M}$ NSCLC model. The combination treatment was more effective at decreasing tumor volume than treatment that only consisted of both Compound IV alone and afatinib alone. Results are shown in FIG. 1.

Example 4

The Effect of Compound IV in Combination with Osimertinib in an EGFR$^{ex19del/T790M}$ PDX NSCLC Model.

Figure 4:
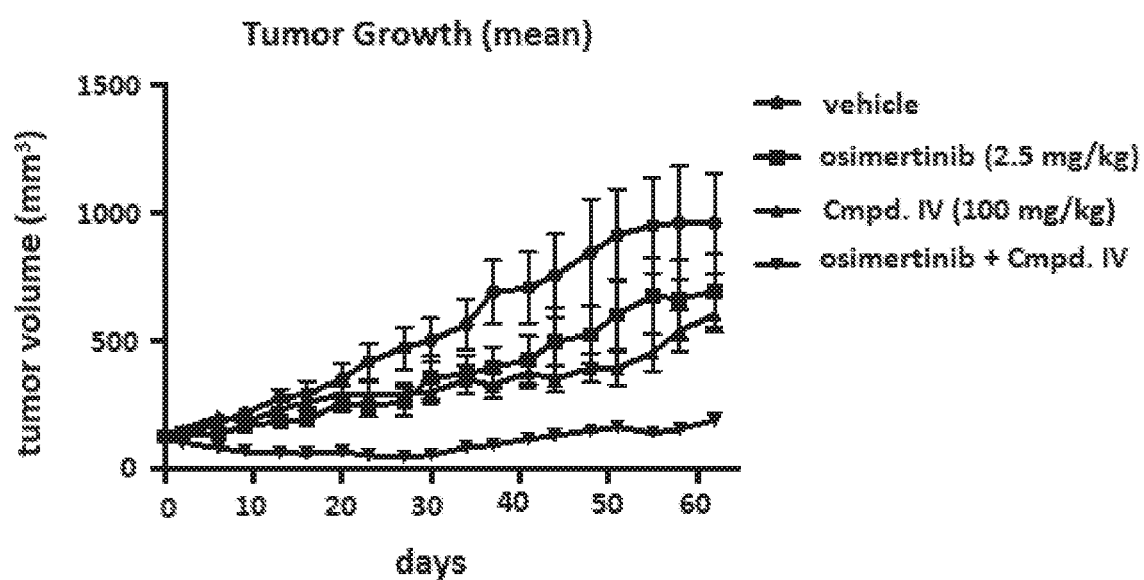
FIG. 4 is a graph showing the combination of a CDK4/6 inhibitor (Compound IV) in combination with a EGFR-TKI (osimertinib) delays tumor growth in an EGFRex19del/T790M patient derived tumor model (TM00219, Jackson Labs). Mice were provided vehicle, osimertinib (2.5 mg/kg), Compound IV (100 mg/kg), or a combination of osimertinib (2.5 mg/kg)+Compound IV (100 mg/kg) orally once daily for 28 days. The x-axis is days from initiation measured in time and the y-axis is mean tumor volume measured in $mm^3$.
Figure 5:
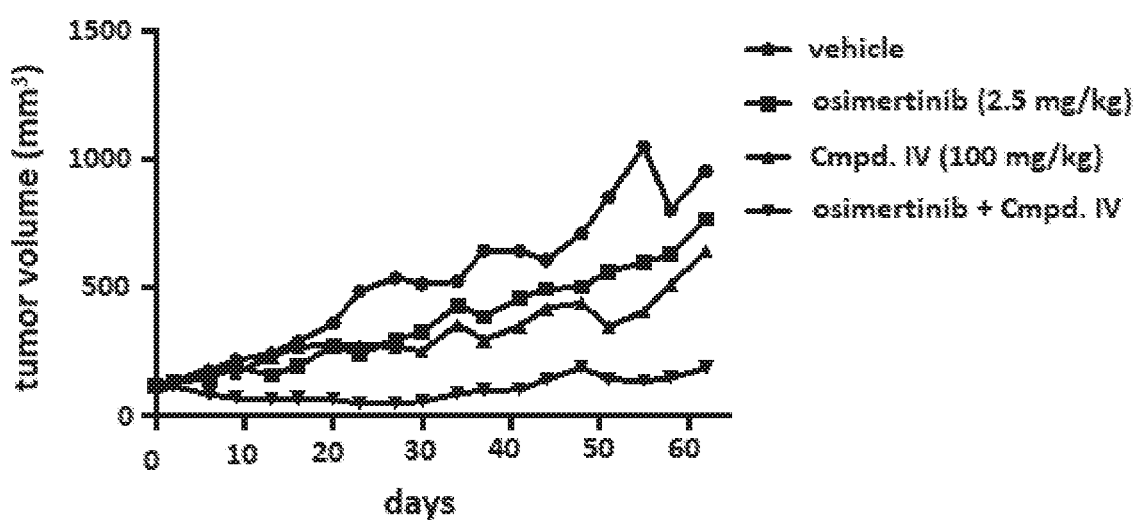
FIG. 5 is a graph showing the combination of a CDK4/6 inhibitor (Compound IV) in combination with a EGFR-TKI (osimertinib) delays tumor growth in an EGFRex19del/T790M patient derived tumor model (TM00219, Jackson Labs). Mice were provided vehicle, osimertinib (2.5 mg/kg), Compound IV (100 mg/kg), or a combination of osimertinib (2.5 mg/kg)+Compound IV (100 mg/kg) orally once daily for 28 days. The x-axis is days from initiation measured in time and the y-axis is median tumor volume measured in $mm^3$.

To study the effect of Compound IV in combination with the EGFR-TKI osimertinib in EGFR T790M+NSCLC, NSG mice were implanted with EGFR$^{ex19del/T790M}$ PDX NSCLC tumor fragments (TM00219, Jackson Labs) and mice were treated and tumors evaluated. Once tumors reached an acceptable treatment size (90-250 mm$^3$), mice were given once daily doses of Compound IV (100 mg/kg), osimertinib (2.5 mg/kg), or the combination by oral gavage for 28 days and tumors were measured every 3 to 4 days. After 28 days tumors continued to be measured until they reached tumor burden (>2000 mm$^3$). The changes in tumor size after treatment with Compound IV+/–osimertinib are presented in FIG. 4 (mean) and FIG. 5 (median). Compared to the vehicle-treated mice, daily treatment with Compound IV or osimertinib showed modest tumor growth inhibition during the 28 days of treatment while the combination treatment caused tumor stasis during dosing that was sustained post treatment indicating that a combination of Compound IV and osimertinib enhances efficacy in EGFR$^{T790M+}$ NSCLC.

Example 5

The Effect of Compound IV in Combination with Osimertinib in an EGFR$^{ex20ins}$ PDX NSCLC Model.

Figure 6:
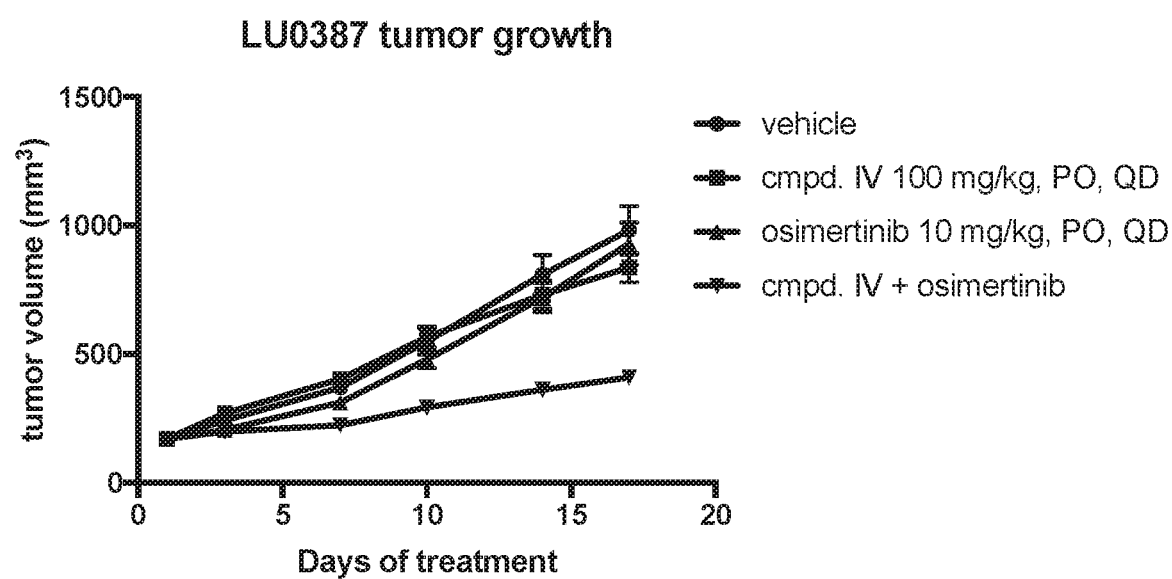
FIG. 6 is a graph showing the combination of a CDK4/6 inhibitor (Compound IV) in combination with a EGFR-TKI (osimertinib) delays tumor growth in an NSCLC tumor model (LU0387) with an Exon20 insertion in EGFR which makes it less sensitive to EGFR-TKI treatment. Mice were provided vehicle, osimertinib (10 mg/kg), Compound IV (100 mg/kg), or a combination of osimertinib (10 mg/kg)+Compound IV (100 mg/kg) orally once daily. The x-axis is days from initiation measured in time and the y-axis is mean tumor volume measured in $mm^3$.

To study the effect of Compound IV in combination with osimertinib in a NSCLC model that has de novo resistance to EGFR inhibitors, BALB/c nude mice were implanted with an EGFR$^{ex20ins}$ PDX NSCLC tumor fragments (LU0387, CrownBio) and mice were then treated and tumors evaluated. Once tumors reached an acceptable treatment size (150-200 mm3), mice were given once daily doses of Compound IV (100 mg/kg), osimertinib (10 mg/kg), or the combination by oral gavage and tumors were measured every 3 to 4 days during treatment. Tumors continued to be measured until they reached tumor burden (>3000 mm3). The changes in tumor size after treatment with Compound IV+/–osimertinib are presented in FIG. 6. Compared to the vehicle-treated mice, daily treatment with Compound IV or osimertinib as single agents did not cause an effect during the 17 days of treatment while the combination cohort demonstrated significant tumor growth delay indicating that a combination of Compound IV and osimertinib enhances efficacy in EGFR-TKI-resistant NSCLC.

Example 6

Safety and Tolerability of Compound IV in Humans.

In Study G1T38-01, single or twice daily (total daily dose split into 2 equal doses, taken every 12 hours) oral doses of Compound IV (G1T38) in the dose range of 3 to 600 mg/day appeared to be well to moderately tolerated in a group of healthy male and female subjects. In most subjects with moderate tolerability, gastrointestinal AEs were the most common moderate intensity treatment-emergent AEs (TE-AEs). Dosing under fed conditions appeared to improve gastrointestinal tolerability. Effects on hematologic parameters were not observed due to the limited duration of dosing. A summary of reported AEs appears below:

| Preferred Term | G1T38-02 (N = 18)[a] | | | | |
|---|---|---|---|---|---|
| | Grade 1-2 n (%) | Grade 3 n (%) | Grade 4 n (%) | Grade 5 n (%) | Overall n (%) |
| Number (%) of patients with any G1T38-related TEAEs | 11 (61.1) | 3 (16.7) | 1 (5.6) | 0 | 15 (83.3) |
| Neutrophil count deceased | 7 (38.9) | 2 (11.1) | 0 | 0 | 9 (50.0) |
| White blood cell count decreased | 7 (38.9) | 0 | 0 | 0 | 7 (38.9) |
| Anaemia | 6 (33.3) | 0 | 0 | 0 | 6 (33.3) |
| Diarrhoea | 5 (27.8) | 0 | 0 | 0 | 5 (27.8) |
| Nausea | 5 (27.8) | 0 | 0 | 0 | 5 (27.8) |
| Neutropenia | 3 (16.7) | 1 (5.6) | 1 (5.0) | 0 | 5 (27.8) |
| Haematuria | 3 (16.7) | 0 | 0 | 0 | 3 (16.7) |
| Vomiting | 3 (16.7) | 0 | 0 | 0 | 3 (16.7) |
| Blood creatinine increased | 2 (11.1) | 0 | 0 | 0 | 2 (11.1) |
| Platelet count decreased | 2 (11.1) | 0 | 0 | 0 | 2 (11.1) |
| Alopecia | 1 (5.6) | 0 | 0 | 0 | 1 (5.6) |
| Blood bilirubin increased | 1 (5.6) | 0 | 0 | 0 | 1 (5.6) |
| Blood lactate dehydrogenase increased | 1 (5.6) | 0 | 0 | 0 | 1 (5.6) |
| Blood urea increased | 1 (5.6) | 0 | 0 | 0 | 1 (5.6) |
| Dry eye | 1 (5.6) | 0 | 0 | 0 | 1 (5.6) |
| Dry mouth | 1 (5.6) | 0 | 0 | 0 | 1 (5.6) |
| Lacrimation increased | 1 (5.6) | 0 | 0 | 0 | 1 (5.6) |
| Leukopenia | 1 (5.6) | 0 | 0 | 0 | 1 (5.6) |
| Monocyte count decreased | 1 (5.6) | 0 | 0 | 0 | 1 (5.6) |
| Stomatitis | 1 (5.6) | 0 | 0 | 0 | 1 (5.6) |
| Thombocytopenia | 1 (5.6) | 0 | 0 | 0 | 1 (5.6) |
| Stomatitis | 1 (5.6) | 0 | 0 | 0 | 1 (5.6) |

AE = adverse event;
CTCAE = Common terminology criteria for adverse events;
TEAE = treatment-emergent adverse event
AEs that started on or after the day of the first dose of study drug were included. AEs with an unknown/not reported onset date were also included. AEs considered by the investigator to be possibly, probably, or definitely related were classified as G1T38-related. Patients with multiple events in the same category were counted only once in that category, at the maximum observed CTCAE grade. Patients with events in more than 1 category were counted once in each of those categories. Number (%) of patients with AEs, sorted by preferred term in decreasing order of frequency (by overall). If the frequencies tied, an alphabetic order was applied. Cumulative data available up to 25 Aug. 2017 was included.

Example 7

Phase I Clinical Trial Combining Compound IV (G1T38) with Osimertinib.

An open-label study of the combination of G1T38 (Compound IV) and osimertinib in patents with EGFR-T790M mutant NSCLC who have failed first-line EGFR-TKI therapy consisting of 2 parts is underway: Part 1 will evaluate the effect of osimertinib on the PK parameters of G1T38 and the safety and tolerability of escalating doses of G1T38 in combination with osimertinib to determine the recommended Phase 2 dose (RP2D); and Part 2 will be a randomized portion to further evaluate the safety, tolerability, and efficacy of the RP2D. Both parts of the study include 3 study phases: Screening Phase, Treatment Phase, and Survival Follow-up Phase. The Treatment Phase begins on the day of the first dose of study drug and completes at the Post-Treatment Visit.

The goals of Part 1 are to determine the effect of osimertinib on the PK parameters of G1T38 and to determine the RP2D of G1T38 in combination with osimertinib by assessing the safety (including DLTs), tolerability, PK, and efficacy of escalating doses of G1T38 administered with osimertinib.

Part 1 Pharmacokinetic Interaction and Dose-Escalation Cohorts

Cohort 1: Six patients will be enrolled in the first cohort in Part 1 to assess the potential effect of osimertinib on the PK parameters of G1T38. Projected dose levels are presented in Table 1. Patients will receive a single oral dose of G1T38 200 mg on Cycle 1 Day −16 and blood samples for G1T38 PK evaluation will be collected over the subsequent 48-hour period. Patients will then receive oral osimertinib 80 mg once daily without G1T38 on Cycle 1 Days −14 to −3, and then both G1T38 and osimertinib on Cycle 1 Day −2, after which blood samples for G1T38 PK evaluation will be collected over the subsequent 48-hour period. Osimertinib once-daily dosing will continue on Cycle 1 Day −1 and through the end of the Treatment Phase. On Cycle 1 Day 1, patients will begin G1T38 once-daily dosing, which will continue through the end of the Treatment Phase (note: there is no Day 0 in the study). DLTs will be evaluated from Cycle 1 Day −16 through Cycle 1 Day 28 (the DLT period). Thereafter, additional sequential dose-escalation cohorts may be enrolled using a standard 3+3 design and will follow the same schedule as described for the first cohort.

| G1T38 Dose Evaluation Criteria | |
|---|---|
| Cohort | G1T38 Dose (mg) |
| 1 | 200 |
| 2 | 300 |
| 3 | 400 |
| 4 | 500 |
| 5 | 600 |

Part 2 Randomized Trial Comparing Osimertinib or G1T38+Osimertinib

In Part 2, eligible patients will be enrolled into a randomized portion of the study. Patients will be randomized (1:1) to receive osimertinib or G1T38 (at the RP2D)+osimertinib. Following screening, patients will begin once daily oral dosing with osimertinib or G1T38+osimertinib on Cycle 1 Day 1.

Patients who are initially randomized to receive osimertinib alone may crossover to G1T38+osimertinib at the time of disease progression as determined by blinded independent central review (BICR). Patients should continue osimertinib monotherapy uninterrupted prior to crossover. The date of crossover is defined as the first date the patient receives G1T38+osimertinib.

Treatments Administered

Study drugs will be administered as follows for each cohort in Part 1 of the study:

Cycle 1 Day −16: single oral dose of G1T38.
Cycle 1 Day −15: no study drug administered.
Cycle 1 Days −14 to −3: oral once-daily doses of osimertinib.
Cycle 1 Day −2: single oral dose of osimertinib and G1T38.
Cycle 1 Day −1: single oral dose of osimertinib.
Beginning with Cycle 1 Day 1, oral once-daily doses of G1T38 and osimertinib will commence.

There is no Day 0 in the study. A treatment cycle is defined as 28 days.

In Part 2, eligible patients will be randomized (1:1) to receive osimertinib or G1T38 (at the RP2D)+osimertinib. Randomized patients will begin once-daily oral dosing of osimertinib or G1T38+osimertinib on Cycle 1 Day 1.

This specification has been described with reference to embodiments of the invention. However, one of ordinary skill in the art appreciates that various modification and changes can be made without departing from the scope of the invention as set forth in the claims below. Accordingly, the specification is to be regarded in an illustrative rather than a restrictive sense, and all such modifications are intended to be included within the scope of the invention.

What is claimed is:

1. A method of treating a human with non-small cell lung cancer (NSCLC) having an epidermal growth factor receptor (EGFR) mutation, wherein the mutation is i) a substitution of threonine with methionine at amino acid 790 (T790M) and ii) a deletion in exon 19 (ex19del), comprising:
administering an effective amount of a cyclin dependent kinase 4/6 (CDK 4/6) inhibitor of the structure:

(Compound VI)

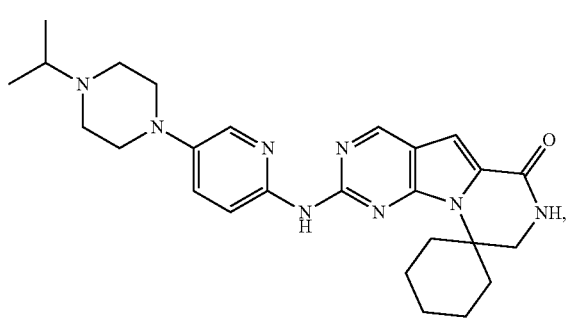

or a pharmaceutically acceptable salt thereof, in combination with an effective amount of an epidermal growth factor receptor tyrosine kinase inhibitor (EGFR-TKI), wherein the EGFR-TKI is osimertinib.

2. The method of claim 1, wherein the CDK4/6 inhibitor and osimertinib are both administered orally at least once daily.

3. The method of claim 1, wherein the NSCLC, prior to administration of the CDK4/6 inhibitor and osimertinib, has developed acquired resistance to a previously administered EGFR-TKI treatment, wherein the acquired resistance developed by the NSCLC is to an EGFR-TKI selected from the group consisting of afatinib, erlotinib, gefitinib, and dacomitinib.

4. A method of treating a human with non-small cell lung cancer harboring an EGFR-activating mutation, wherein the EGFR activating mutation is an exon 19 deletion (ex19del), comprising administering an effective amount of a cyclin dependent kinase 4/6 (CDK 4/6) inhibitor of the structure:

(Compound IV)

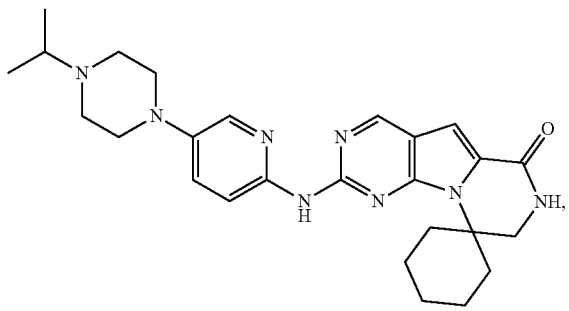

or a pharmaceutically acceptable salt thereof, in combination with an effective amount of an EGFR-TKI, wherein the EGFR-TKI is osimertinib.

5. The method of claim 4, wherein at the time of administration of the CDK4/6 inhibitor and osimertinib, the human has not previously been administered an EGFR-TKI.

6. The method of claim 4, wherein the CDK4/6 inhibitor and osimertinib are both administered orally at least once daily.

7. The method of claim 4, wherein the exon 19 deletion comprises a deletion of amino acids leucine, arginine, glutamic acid, and alanine (LREA).

* * * * *